United States Patent
Inoue et al.

(10) Patent No.: US 10,429,238 B2
(45) Date of Patent: Oct. 1, 2019

(54) OPTICAL MEASUREMENT METHOD AND OPTICAL MEASUREMENT APPARATUS

(71) Applicant: Otsuka Electronics Co., Ltd., Osaka (JP)

(72) Inventors: Nobuyuki Inoue, Kyoto (JP); Taku Nagashima, Kusatsu (JP)

(73) Assignee: Otsuka Electronics Co., Ltd., Osaka (JP)

( * ) Notice: Subject to any disclaimer, the term of this patent is extended or adjusted under 35 U.S.C. 154(b) by 108 days.

(21) Appl. No.: 15/677,606

(22) Filed: Aug. 15, 2017

(65) Prior Publication Data
US 2018/0073923 A1 Mar. 15, 2018

(30) Foreign Application Priority Data
Sep. 9, 2016 (JP) .................................. 2016-176777

(51) Int. Cl.
*G01J 3/02* (2006.01)
*G01N 21/27* (2006.01)
(Continued)

(52) U.S. Cl.
CPC ............. *G01J 3/027* (2013.01); *G01J 3/0218* (2013.01); *G01J 3/0221* (2013.01);
(Continued)

(58) Field of Classification Search
CPC ........ G01J 3/027; G01J 3/0218; G01J 3/0221; G01J 3/0264; G01J 3/28; G01J 3/2803; G01N 21/359
See application file for complete search history.

(56) References Cited

U.S. PATENT DOCUMENTS 5,272,518 A * 12/1993 Vincent .................... G01J 3/12
250/226
2004/0034494 A1 2/2004 Wada et al.
(Continued)

FOREIGN PATENT DOCUMENTS

JP 2005-033633 A 2/2005
JP 2006-023284 A 1/2006
(Continued)

OTHER PUBLICATIONS

Bean et al., Ground-based transit spectroscopy of the hot-jupiter WASP-19b in the near-infrared, Jul. 10, 2013, The Astrophysical Journal, vol. 771, No. 2, pp. 1-12 (Year: 2013).*
(Continued)

*Primary Examiner* — David P Porta
*Assistant Examiner* — Jeremy S Valentiner
(74) *Attorney, Agent, or Firm* — Studebaker & Brackett PC

(57) ABSTRACT

There is provided an optical measurement method using a detector having a detection sensitivity to at least a near-infrared region. The optical measurement method including: obtaining an output value by measuring a light sample at any exposure time with the detector; and correcting the output value with an amount of correction corresponding to the output value, when the exposure time at which the output value is obtained is within a second range. The amount of correction includes a product of a coefficient and a square of the exposure time, the coefficient indicating a degree to which an output value obtained when the light sample is measured with the detector at an exposure time within the second range deviates from output linearity obtained when the light sample is measured with the detector at an exposure time within a first range.

5 Claims, 14 Drawing Sheets

(51) Int. Cl.
*G01J 3/28* (2006.01)
*G01N 21/359* (2014.01)

(52) U.S. Cl.
CPC .............. *G01J 3/0264* (2013.01); *G01J 3/28* (2013.01); *G01J 3/2803* (2013.01); *G01N 21/274* (2013.01); *G01J 2003/2876* (2013.01); *G01N 21/359* (2013.01)

(56) References Cited

U.S. PATENT DOCUMENTS

2004/0076325 A1    4/2004  Wada et al.
2005/0128475 A1*  6/2005  Imura ...................... G01J 1/08
    356/300

FOREIGN PATENT DOCUMENTS

WO        02/39076 A1    5/2002
WO        02/39094 A1    5/2002

OTHER PUBLICATIONS

Kasumi—JP 2006-023284 A—English Translation obtained Jan. 22, 2019 from Google Patents (Year: 2019).*

* cited by examiner

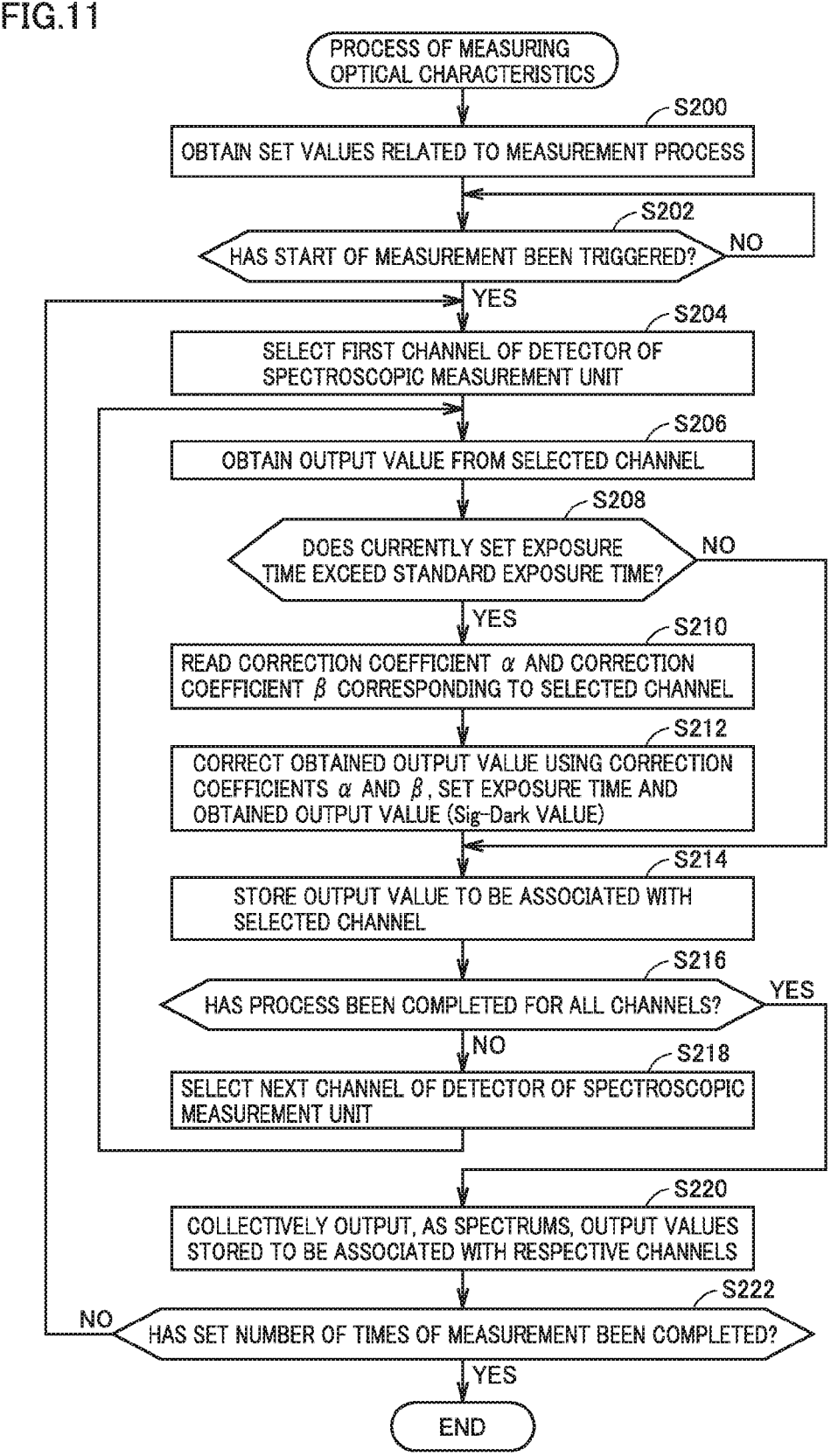

Sig-Dark (AFTER CORRECTION)

LIGHT RECEPTION SENSITIVITY RATIO
(AFTER CORRECTION)

US 10,429,238 B2

OPTICAL MEASUREMENT METHOD AND OPTICAL MEASUREMENT APPARATUS

BACKGROUND OF THE INVENTION

Field of the Invention

The present invention relates to an optical measurement method and an optical measurement apparatus that can enhance the measurement accuracy.

Description of the Background Art

A configuration of receiving light from a sample at a detector is used in a general optical characteristic measurement system. In order to enhance the measurement accuracy, it is preferable that there is a stable correspondence relation (particularly, output linearity) between the intensity of the light incident on the detector and the signal level output from the detector.

In reality, fluctuations occur in the correspondence relation due to uncertainty and the like of an element forming the detector. Therefore, a method for correcting an error caused by such fluctuations has been proposed.

For example, Japanese Patent Laying-Open No. 2006-23284 discloses a detection apparatus for a spectrophotometer that has a sufficient sensitivity to the entire range of the ultraviolet region, the visible light region and the near-infrared region, and ensures sufficient linearity. This detection apparatus for the spectrophotometer has a photomultiplier tube detector, an InGaAs detector and a PbS detector as well as a switch configured to perform switching among these detectors, and is further provided with output conversion means for correcting a difference in output linearity among the detectors.

Japanese Patent Laying-Open No. 2005-33633 discloses a linearity correction apparatus for a CCD (Charge Coupled Device) camera that may divide a CCD imaging region serving as an imaging element into blocks, output a video signal independently for each block, and automatically correct a difference in output level linearity among the blocks.

WO2002/039076 discloses a method for performing measurement by applying light to an object to be measured and receiving, at a sensor, the light reflected from a detection subject portion. In this measurement method, a sensor not having output linearity with respect to an amount of received light is used as the sensor, and linearization process is performed to correct an output of the sensor such that the output of the sensor when the amount of received light at the sensor is varied is proportional to the amount of received light.

WO2002/039094 discloses a measurement method in which linearization correction and light unevenness correction are performed. The linearization correction is for correcting an output of an image sensor such that the output of the image sensor is proportional to an amount of incident light, and the light unevenness correction is for correcting each pixel output of the image sensor such that each pixel output subjected to linearization correction becomes uniform when a reference object is measured.

The above-described conventional art still has the following problems.

In the detection apparatus for the spectrophotometer disclosed in Japanese Patent Laying-Open No. 2006-23284, switching among the three types of detectors is performed, such that an excellent sensitivity and an excellent S/N ratio are obtained particularly in the intermediate wavelength region. However, preparation of the three types of detectors is required, and Japanese Patent Laying-Open No. 2006-23284 does not teach improvement in output linearity of each detector.

The linearity correction apparatus for the CCD camera disclosed in Japanese Patent Laying-Open No. 2005-33633 is the technique directed to a general video camera and cannot be directly applied to an optical characteristic measurement system.

In the linearization process performed in the method disclosed in WO2002/039076, preliminarily prepared linearization data is required. This linearization data is created by preparing N types (e.g., 11 types) of reference plates having different reflectances, and associating imaging data obtained by imaging each reference plate with a known reflectance of each reference plate. Such step of creating the linearization data is complicated.

In the linearization correction performed in the measurement method disclosed in WO2002/039094, correction reference data is used. The process for obtaining this correction reference data includes the process of obtaining a voltage value of a photodetector when the brightest pixel in an image obtained by imaging a white plate reaches a saturated light amount, the process of dividing the obtained voltage value into twenty equal parts to obtain 21-stage voltage values, and imaging the white plate at the respective light amounts and storing pieces of data, the offset process for all pieces of image data, the process of averaging the values of the five pixels continuously arranged near the brightest pixel in the image, and the like. As described above, the process for obtaining the correction reference data is complicated.

SUMMARY OF THE INVENTION

There has been a demand for an optical measurement method and an optical measurement apparatus with reduced time and effort for calibration required at the time of measurement and with enhanced accuracy of output linearity.

According to an embodiment of the present invention, there is provided an optical measurement method using a detector having a detection sensitivity to at least a near-infrared region. A first range of exposure time in which an output value from the detector is proportional to an intensity of light incident on the detector, and a second range of exposure time in which the output value from the detector is not proportional to the intensity of the light incident on the detector are obtained preliminarily. The optical measurement method includes: obtaining an output value by measuring a light sample at any exposure time with the detector; and correcting the output value with an amount of correction corresponding to the output value, when the exposure time at which the output value is obtained is within the second range. The amount of correction includes a product of a coefficient and a square of the exposure time, the coefficient indicating a degree to which an output value obtained when the light sample is measured with the detector at an exposure time within the second range deviates from output linearity obtained when the light sample is measured with the detector at an exposure time within the first range.

The coefficient may be determined based on the output value, the exposure time at which the output value is obtained, and a predetermined correction coefficient.

The optical measurement method may further include: obtaining output values by measuring a light sample having a prescribed light intensity at a plurality of exposure times with the detector, the plurality of exposure times including an exposure time within the first range and a plurality of exposure times within the second range; determining a set of coefficients that define an approximate equation for the obtained output values; varying the intensity of the light incident on the detector, and repeating the step of obtaining the output values and the step of determining the set of coefficients; and determining the correction coefficient by regression analysis of the obtained sets of coefficients for the respective light intensities.

The set of coefficients may include a coefficient of a linear term of the approximate equation and a coefficient of a quadratic term of the approximate equation. The step of determining the correction coefficient may include performing the regression analysis while the coefficient of the linear term is fixed as a value by using the output value from the detector at the exposure time within the first range, which is used to determine an approximate equation corresponding to the first range.

The detector may have a plurality of channels sectioned in units of a prescribed wavelength width. The correction coefficient may be determined for each channel.

The detector may include an InGaAs linear image sensor.

An optical measurement apparatus according to the embodiment of the present invention includes: a detector having a detection sensitivity to at least a near-infrared region; and a controller configured to be able to refer to a predetermined correction coefficient. The controller is configured to: obtain an output value by measuring a light sample at any exposure time with the detector; output the output value as it is, when the exposure time at which the output value is obtained is within a predetermined range; and correct the output value with an amount of correction to output the corrected output value, when the exposure time at which the output value is obtained is not within the predetermined range, the amount of correction including a value obtained by multiplying a coefficient by a square of the exposure time, the coefficient being determined based on the output value, the exposure time at which the output value is obtained, and the correction coefficient.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 11 is a flowchart showing a process procedure of a measurement method using the optical measurement apparatus according to the present embodiment.

DESCRIPTION OF THE PREFERRED EMBODIMENTS

Figure 1:
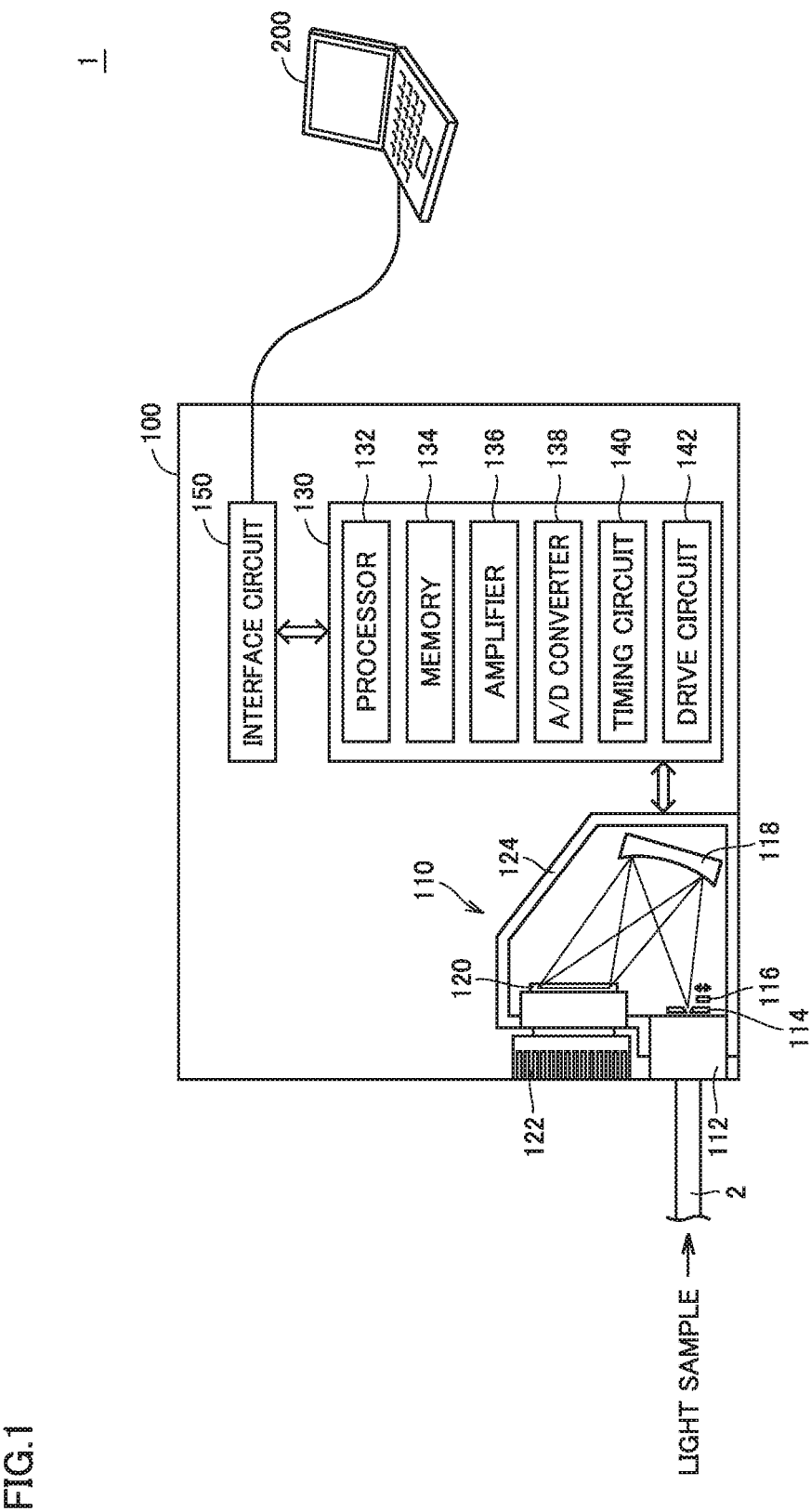
FIG. 1 is a schematic diagram showing an apparatus configuration of an optical measurement system according to the present embodiment.

An embodiment of the present invention will be described in detail with reference to the drawings, in which the same or corresponding portions are denoted by the same reference characters and description thereof will not be repeated.

<A. Apparatus Configuration>

First, an apparatus configuration of an optical measurement system including an optical measurement apparatus according to the present embodiment will be described.

(a1: Optical Measurement System)

Referring to FIG. 1, an optical measurement system 1 includes an optical measurement apparatus 100 and a processing apparatus 200. Optical measurement system 1 may further include a printer configured to print out a measurement result and the like. Although FIG. 1 shows the example in which optical measurement apparatus 100 and processing apparatus 200 are separated from each other, these apparatuses may be integrally formed. Alternatively, a plurality of optical measurement apparatuses 100 may be controlled by single processing apparatus 200.

Optical measurement system 1 can measure various optical characteristics. Examples of the optical characteristics include a total amount of light flux, an illuminance (or spectral irradiance), a brightness (or spectral radiance), a light intensity, color rendering (a chromaticity coordinate, an excitation purity, a correlated color temperature, and color rendering properties), an absorptivity, a transmittance, a reflectance, an emission spectrum (and a peak wavelength and a half-wave value), an excitation spectrum, external quantum efficiency (or external quantum yield), internal quantum efficiency (or internal quantum yield) and the like.

Hereinafter, a configuration that can measure optical characteristics in the near-infrared region (wavelength range: about 800 to 2500 [nm]) will be described as one example of optical measurement system 1 and optical measurement apparatus 100 according to the present embodiment. Optical measurement system 1 according to the present embodiment can perform measurement using either a reflection method or a transmission method, and can also measure a sample itself when the sample is a self-light-emitting sample.

(a2: Optical Measurement Apparatus)

Optical measurement apparatus 100 according to the present embodiment has a detector having a detection sensitivity to at least the near-infrared region. A configuration that can perform spectroscopic measurement (multichannel) will be described as a typical example of optical measurement apparatus 100. However, the optical measurement method including the process of correcting the output linearity according to the present embodiment is also applicable to a so-called monochromator that detects a light intensity and the like in a particular wavelength or wavelength range.

Optical measurement apparatus 100 includes a spectroscopic measurement unit 110, a controller 130 and an interface or interface circuit 150.

Spectroscopic measurement unit 110 receives light (hereinafter also referred to as "light sample") input from a sample through an optical fiber 2, and outputs an intensity distribution (intensity spectrum) of each wavelength component included in the light sample. More specifically, spectroscopic measurement unit 110 includes a connection unit 112, an optical slit 114, a shutter 116, a diffraction grating 118, a detector 120, and a cooling fin 122. Optical slit 114, shutter 116, diffraction grating 118, and detector 120 are arranged in a housing 124.

One end of optical fiber 2 is fixed to housing 124 by connection unit 112. Connection unit 112 fixes optical fiber 2 such that an optical axis of an open end of optical fiber 2 is aligned with a central axis of optical slit 114. The light sample transmitted through optical fiber 2 passes through optical slit 114 and enters diffraction grating 118. Optical slit 114 adjusts a cross-sectional diameter of the light sample. Shutter 116 optically connects/disconnects optical fiber 2 to/from diffraction grating 118. During normal measurement, shutter 116 is maintained in the open state, such that the light sample emitted from optical fiber 2 enters diffraction grating 118. On the other hand, during calibration, shutter 116 is maintained in the closed state, such that entry of the light sample emitted from optical fiber 2 to diffraction grating 118 is blocked.

When the light sample emitted from optical fiber 2 enters diffraction grating 118, diffraction grating 118 optically separates the light sample into respective wavelength components. Namely, the light sample is diffracted in accordance with a pattern formed on a surface of diffraction grating 118, and thus, the respective wavelength components included in the light sample travels in different directions corresponding to the wavelengths. The respective wavelength components enter detector 120 optically aligned with diffraction grating 118. As described above, diffraction grating 118 is arranged to be associated with detector 120 and is configured to guide the light in the prescribed wavelength range (in this configuration example, the near-infrared region) to detector 120. A blazed diffraction grating and the like can be used as diffraction grating 118.

A one-dimensional array element (such as, for example, a line sensor) or a two-dimensional array element (such as, for example, a CCD image sensor or a CMOS image sensor) formed by a plurality of independent detection arrayed surfaces is used as detector 120 such that detector 120 can receive the respective wavelength components separated by diffraction grating 118. A CCD (Charge-Coupled Device) image sensor may be used as detector 120. The length, the resolution and the like of the detection surfaces of detector 120 are designed depending on the diffraction property of diffraction grating 118 and the wavelength range of the light to be detected.

Detector 120 has a detection sensitivity to at least the near-infrared region. A device made of InGaAs (indium gallium arsenide), GaAs (gallium arsenide), GaSb (gallium antimony), InAs (indium arsenide), InSb (indium antimony), PbS (lead sulfide), PbSe (lead selenide) or the like can be used as such detection element having a detection sensitivity to the near-infrared region. In the present embodiment, an InGaAs linear image sensor formed by two-dimensionally arranging InGaAs photodiodes is used by way of example. Detector 120 includes an InGaAs photodiode array, a charge amplifier, a sample-and-hold circuit, an address switch, a shift register, an offset compensation circuit and the like. Detector 120 is arranged to be located in the diffraction direction of diffraction grating 118, and thus, has a plurality of channels sectioned in units of a prescribed wavelength width. Detector 120 further has a read circuit configured to read a detected value at a specified channel of the InGaAs linear image sensor.

The side opposite to the detection surfaces of detector 120 is mechanically connected to cooling fin 122 arranged outside housing 124, so as to reduce thermal noise occurring at detector 120. A not-shown electronic cooling apparatus (e.g., a Peltier element) may be arranged between cooling fin 122 and detector 120.

Controller 130 performs the process required for optical measurement in spectroscopic measurement unit 110. Typically, controller 130 performs the operation of opening and closing shutter 116 in spectroscopic measurement unit 110, activation of detector 120, the signal processing (such as amplification processing and noise removal) for an output signal output from detector 120, the correction process for improving the output linearity of the output signal output from detector 120, and the like.

More specifically, controller 130 includes a processor 132, a memory 134, an amplifier 136, an A/D (Analog to Digital) converter 138, a timing circuit 140, and a drive circuit 142.

Processor 132 executes a program, thereby implementing the process required in optical measurement apparatus 100. Instead of processor 132, the process may be implemented by a hard-wired configuration such as ASIC (Application Specific Integrated Circuit). Memory 134 stores the program executed by processor 132, data required for the below-described correction process, and the like.

Amplifier 136 amplifies the output signal output from detector 120. A/D converter 138 is arranged in a stage subsequent to amplifier 136, and periodically samples the output signal (analog signal) and sequentially outputs a digital value indicating a signal intensity at each timing. Timing circuit 140 sequentially drives the detection element forming detector 120, and provides the timing of driving the detection element to A/D converter 138. Timing circuit 140 adjusts the occurrence cycle or phase of the timing in accordance with the specified exposure time.

Drive circuit 142 switches the position of shutter 116, thereby implementing the opening and closing operation.

Interface or interface circuit 150 serves as an intermediary of access from processing apparatus 200 to optical measurement apparatus 100. For example, a general-purpose configuration such as USB (Universal Serial Bus) or Ethernet (registered trademark) may be used as interface or interface circuit 150.

Figure 2:
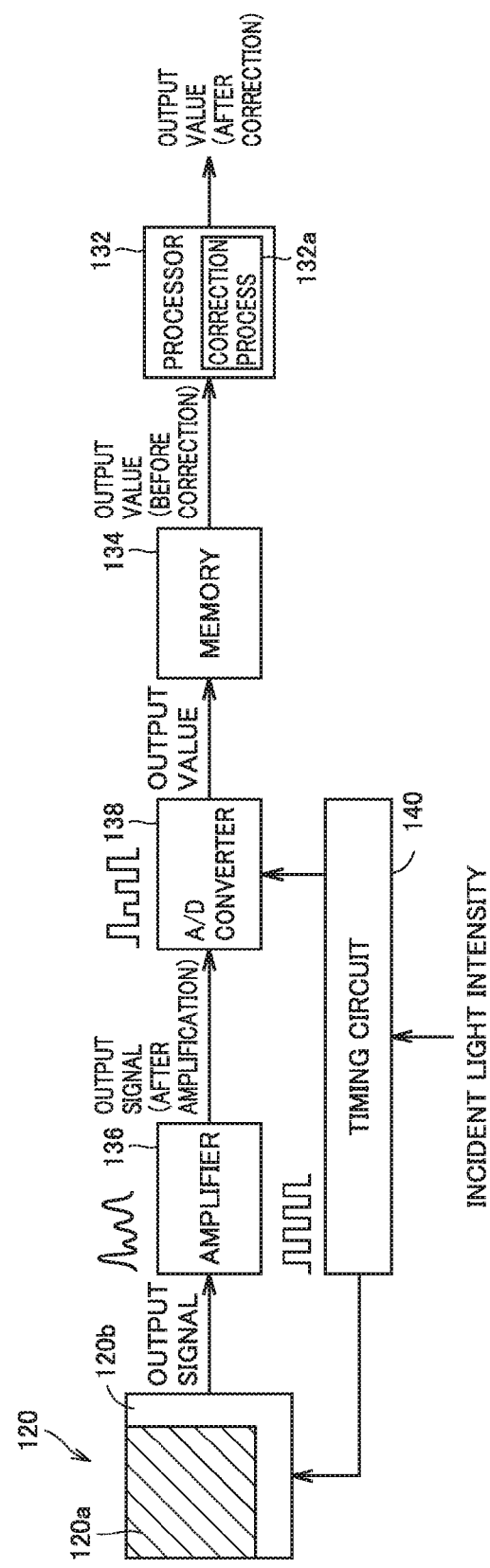
FIG. 2 is a block diagram showing a configuration related to the detection process in an optical measurement apparatus according to the present embodiment.

Referring to FIG. 2, detector 120 includes an InGaAs photodiode array 120a and a read circuit 120b configured to read a detected value at any channel of InGaAs photodiode array 120a. In response to a clock signal of a prescribed cycle generated by timing circuit 140, read circuit 120b cyclically outputs a detected value at each channel of InGaAs photodiode array 120a. Amplifier 136 amplifies the output signal output from read circuit 120b, and outputs the amplified output signal to A/D converter 138. A/D converter 138 samples the input amplified output signal at every prescribed cycle, and sequentially outputs an output value indicating the intensity of the output signal at each sampling cycle. In response to the clock signal provided from timing circuit 140, A/D converter 138 resets samples stored therein. Namely, based on the clock signal provided from timing circuit 140, A/D converter 138 synchronizes the start of output of the output signal from read circuit 120b and the reset of sampling in A/D converter 138. The output value from A/D converter 138 is sequentially stored in memory 134.

Processor 132 reads the output value (before correction) sequentially stored in memory 134, and performs an output linearity correction process 132a. Details of output linearity correction process 132a will be described below. A corrected output value obtained as a result of output linearity correction process 132a performed by processor 132 is output to processing apparatus 200 and the like.

(a3: Processing Apparatus 200)

Processing apparatus 200 processes the measurement result provided from optical measurement apparatus 100 and thereby calculates various optical characteristics of the light sample. Processing apparatus 200 is typically implemented by a general-purpose computer.

Figure 3:
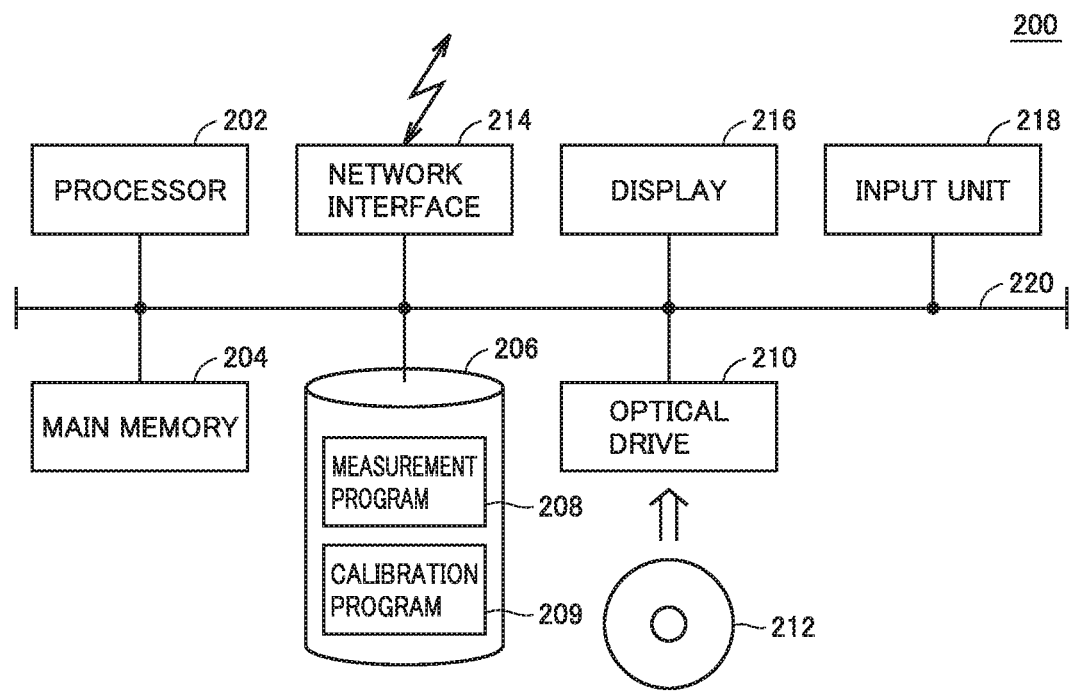
FIG. 3 is a schematic diagram showing an apparatus configuration of a processing apparatus according to the present embodiment.

Referring to FIG. 3, processing apparatus 200 includes a processor 202 configured to execute various programs including the operating system (OS), a main memory 204 configured to temporarily store data required for execution of the programs by processor 202, and a hard disk 206 configured to store the programs executed by processor 202 in a non-volatile manner. The components forming optical measurement apparatus 100 are connected to one another by a bus 220.

A measurement program 208 for calculating various optical characteristics from the light sample, a calibration program 209 for implementing the calibration process in optical measurement apparatus 100, and the like are prestored in hard disk 206. Measurement program 208 and/or calibration program 209 is/are stored in an optical medium 212 such as DVD (Digital Versatile Disc) and distributed, or is/are distributed via the network. When measurement program 208 and/or calibration program 209 is/are stored in optical medium 212 and distributed, measurement program 208 and/or calibration program 209 is/are read by an optical drive 210 and installed onto hard disk 206. On the other hand, when measurement program 208 and/or calibration program 209 is/are distributed via the network, measurement program 208 and/or calibration program 209 is/are received via a network interface 214 and installed onto hard disk 206.

A display 216 displays the calculated optical characteristics, the operating condition of optical measurement apparatus 100, and the like. An input unit 218 typically includes a keyboard, a mouse and the like, and accepts the user's operation.

All or a part of the functions of processing apparatus 200 may be implemented by a hard-wired configuration.

<B. Method for Correcting Output Linearity>

Next, description will be given of degradation in output linearity occurring at detector 120 and a method for correcting such degradation in output linearity, which have been found by the inventors of the present application.

(b1: Overview)

Figure 4:
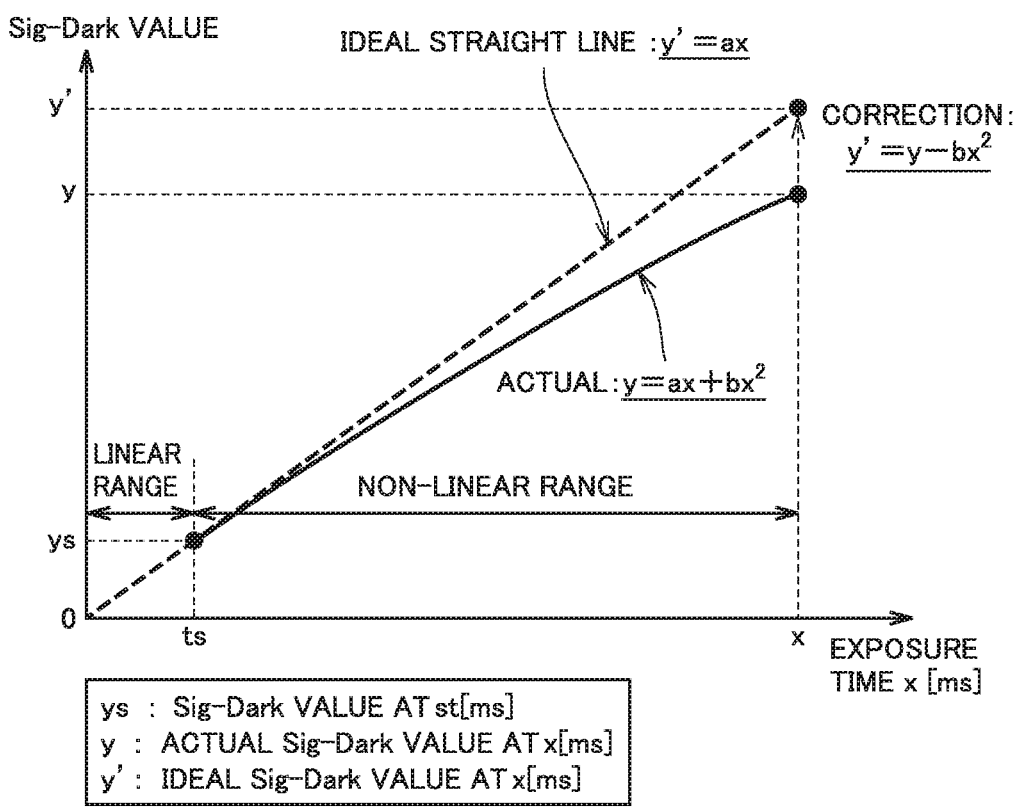
FIG. 4 is a diagram for describing an overview of a method for correcting the output linearity with respect to an output signal output from a detector according to the present embodiment.

FIG. 4 is a diagram for describing an overview of a method for correcting the output linearity with respect to the output signal output from detector 120 according to the present embodiment. FIG. 4 shows a relation between the exposure time of detector 120 and the output signal output from detector 120. Specifically, suppose ys represents a dark-corrected output value (hereinafter also denoted as "Sig-Dark value") output from detector 120 at a certain standard exposure time ts [ms]. While the magnitude of standard exposure time ts depends on the element properties of detector 120, standard exposure time ts is set at 10 [ms], for example.

The dark-corrected output value (Sig-Dark value) will now be described. Even when shutter 116 (see FIG. 1) is closed to interrupt the entry of the light to detector 120, the output signal is not zero due to thermal noise and the like at detector 120. The output signal in this state will also be referred to as "dark output". A difference with respect to the dark output should be evaluated as the substantial magnitude of the output signal output from detector 120. Namely, a value (Sig-Dark value) obtained by subtracting the preliminarily obtained dark output (Dark) from the output value (Sig) output from detector 120 is used as the output value from detector 120.

Suppose the exposure time of detector 120 increases from ts [ms] to x [ms]. In proportion to the increase in exposure time, a summed value of the amount of light incident on detector 120 increases. Therefore, a Sig-Dark value y' output from detector 120 at exposure time x should ideally be equal to ys×x/ts. Namely, it is ideal that Sig-Dark value y' output from detector 120 is proportional to exposure time x, i.e., the relation of y'=ax is maintained.

In reality, however, as the exposure time increases, the output signal output from detector 120 falls below the ideal straight line. According to the findings by the applicants of the present application, an actual Sig-Dark value y output from detector 120 can be defined by a quadratic equation for exposure time x, i.e., $y=ax+bx^2$.

The two equations are now compared. Then, a coefficient a of a linear term for exposure time x is common to actual Sig-Dark value y and ideal Sig-Dark value y', and only a quadratic term for exposure time x corresponds to an amount of deviation from the output linearity.

As described above, the inventors of the present application have obtained the new findings that, by correcting a signal intensity corresponding to the quadratic term ($bx^2$) for exposure time x, the output linearity of the output signal output from detector 120 with respect to the exposure time can be maintained. In other words, the inventors of the present application have found that, by applying the correction equation of $y'=y-bx^2$ to actual Sig-Dark value y, ideal Sig-Dark value (corrected Sig-Dark value) y' can be calculated.

Based on these new findings, the method for correcting the output linearity according to the present embodiment provides the optical measurement apparatus that achieves the output linearity, in combination with the process of determining coefficient a and coefficient b, and the like.

(b2: Measurement Result)

One example of a measurement result according to the above-described new findings is shown. Specifically, an InGaAs linear image sensor (manufactured by Hamamatsu Photonics K.K.; model No. G9206-256W; total number of pixels: 256) was used as detector 120. One example of a measurement result obtained when the exposure time and the incident light intensity of the InGaAs linear image sensor are each varied is shown.

Figure 5A:
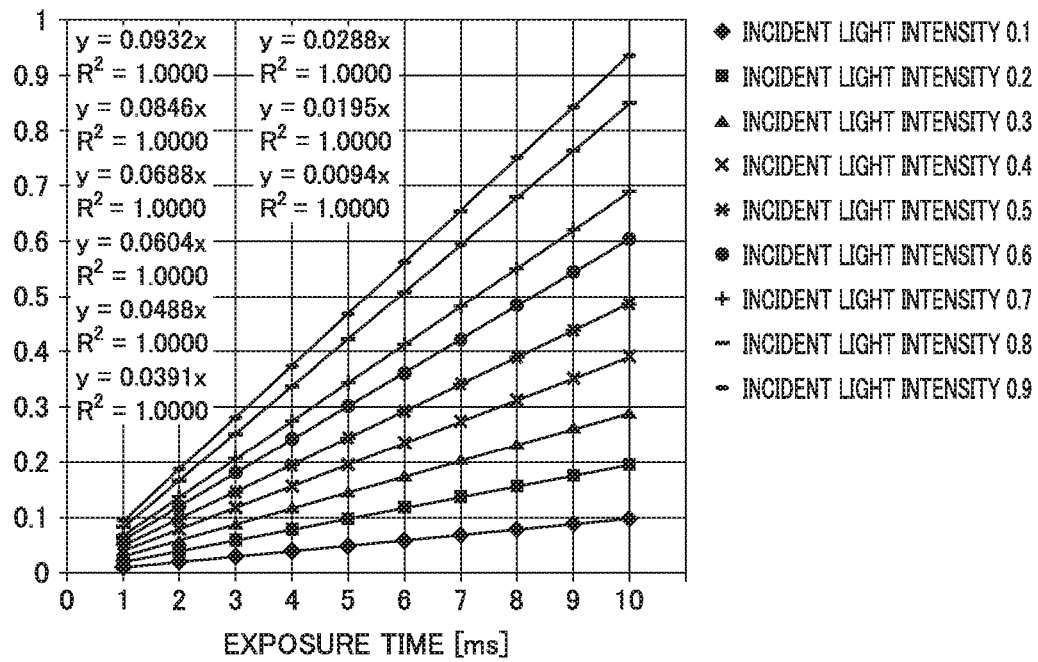
FIGS. 5A and 5B are diagrams showing one example of measurement results when the exposure time is varied within the range of 1 to 10 [ms].
Figure 5B:
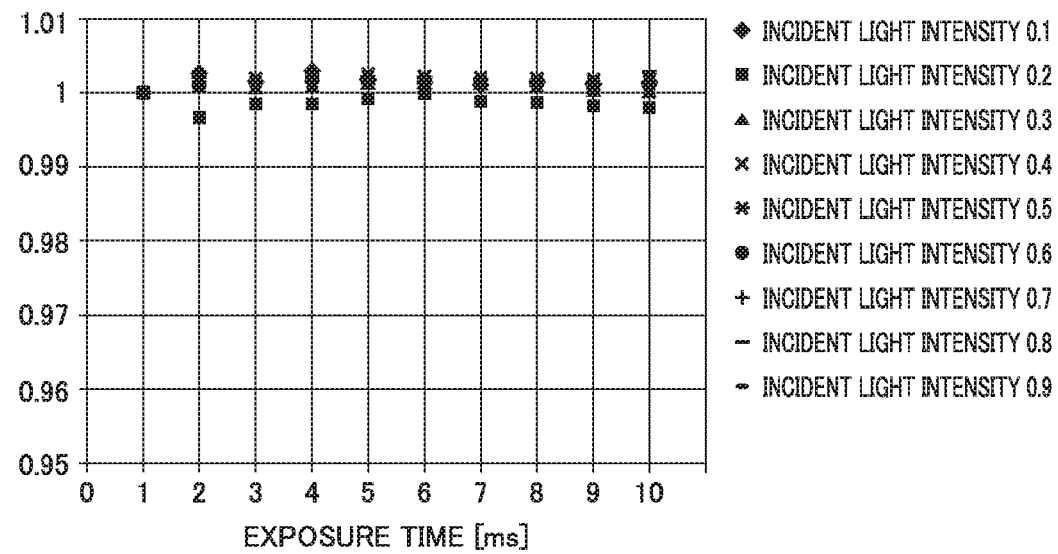
Figure 6A:
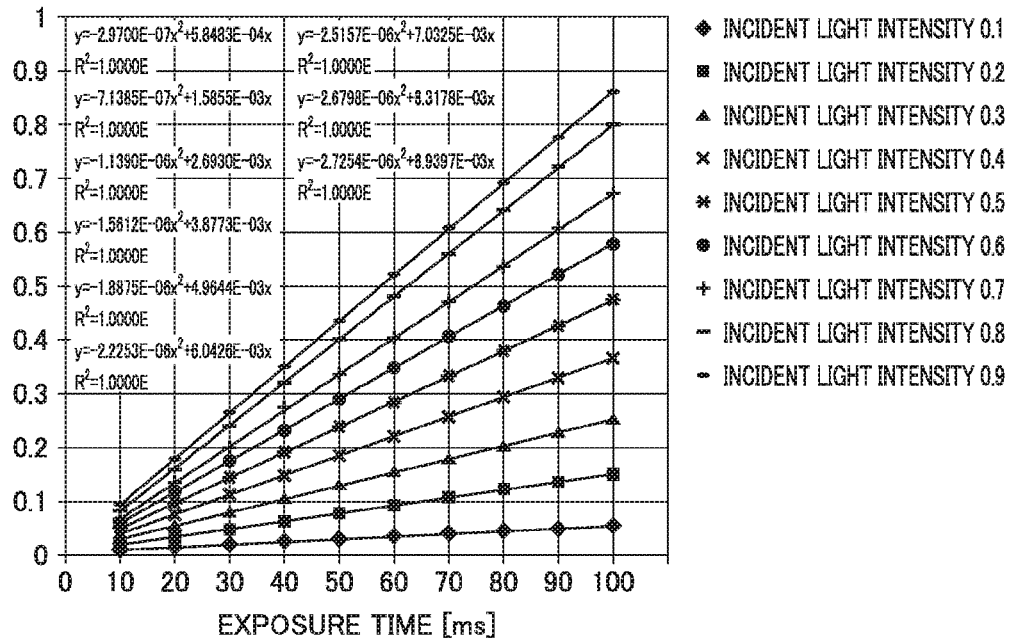
FIGS. 6A and 6B are diagrams showing one example of measurement results when the exposure time is varied within the range of 10 to 100 [ms].
Figure 6B:
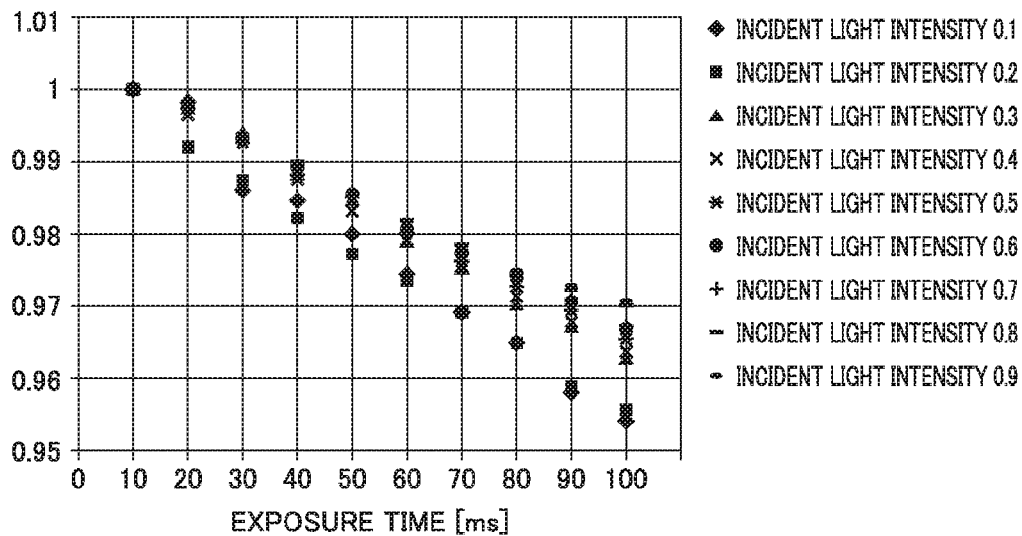

FIGS. 5A and 5B show one example of measurement results when the exposure time is varied within the range of 1 to 10 [ms]. FIGS. 6A and 6B show one example of measurement results when the exposure time is varied within the range of 10 to 100 [ms]. By way of example, FIGS. 5A, 5B, 6A, and 6B show the case in which standard exposure time is shown in FIG. 4 is 10 [ms].

In FIGS. 5A, 5B, 6A, and 6B, the incident light intensity is defined by the relative values ranging from 0.1 to 0.9. A positional relation between optical fiber 2 and a light source emitting the light sample was adjusted such that the output value at the shortest exposure time (1 [ms] in FIGS. 5A and 5B, and 10 [ms] in FIGS. 6A and 6B) fell within approximately 10% of the output range in each of FIGS. 5A, 5B, 6A, and 6B.

In FIGS. 5A and 6A, the actual Sig-Dark value at each exposure time is plotted for each incident light intensity. In addition, a regression equation obtained by regression analysis of the plot sets for each incident light intensity, and a value of a corresponding determination coefficient $R^2$ are shown.

In FIGS. 5B and 6B, the light reception sensitivity ratio at each exposure time is plotted for each incident light intensity. Herein, a value obtained by dividing the actual Sig-Dark value by the exposure time is defined as "light reception sensitivity", and a value obtained by dividing "light reception sensitivity" at each exposure time by the reference exposure time is defined as "light reception sensitivity ratio". The shortest exposure time in each graph is used as the reference exposure time. Namely, in each measurement result, the light reception sensitivity ratio is calculated as follows:

(1) exposure time ranging from 1 to 10 [ms]: linear range light reception sensitivity ratio={(actual Sig-Dark value at exposure time x [ms])/(exposure time x [ms])}/{(actual Sig-Dark value at exposure time of 1 [ms])/(exposure time of 1 [ms])}

(2) exposure time ranging from 10 to 100 [ms]: non-linear range light reception sensitivity ratio={(actual Sig-Dark value at exposure time x [ms])/(exposure time x [ms])}/{(actual Sig-Dark value at exposure time of 10 [ms])/(exposure time of 10 [ms])}.

In other words, the light reception sensitivity ratio indicates a degree to which the Sig-Dark value at the exposure time other than the shortest exposure time deviates from the straight line connecting the origin point and the Sig-Dark value at the shortest exposure time in FIGS. 5A and 5B.

As the light reception sensitivity ratio gets closer to 1, the output linearity becomes higher. When the ideal output linearity is maintained, the light reception sensitivity ratio is constantly 1 regardless of the exposure time.

Referring to FIG. 5A, when the exposure time is 1 to 10 [ms], a regression equation in the form of a linear equation (y=ax+b) is obtained for all incident light intensities, and determination coefficient $R^2$ is 1. Namely, it can be determined that the output linearity is completely maintained when the exposure time is 1 to 10 [ms].

Referring to FIG. 5B, it can be seen that when the exposure time is 1 to 10 [ms], the light reception sensitivity ratio falls within the range of 0.99 to 1.01 (i.e., deviation from the ideal straight line is within ±1%) for all incident light intensities and thus the excellent output linearity is obtained.

In contrast, when the exposure time exceeds 10 [ms], the output linearity is not maintained. Referring to FIG. 6A, when the exposure time is 10 to 100 [ms], a regression equation in the form of a quadratic equation (y=ax²+bx+c), not the regression equation in the form of the linear equation (y=ax+b), is obtained for all incident light intensities, and determination coefficient $R^2$ for the regression equation in the form of the quadratic equation is 1. This means that when the exposure time is 10 to 100 [ms], the output linearity is not maintained and the output value at each exposure time can be estimated with a high degree of accuracy in accordance with the quadratic equation.

More specifically, when the exposure time is 10 to 100 [ms], actual Sig-Dark value y' can be approximated using the following equation (1):

$$y'(s,x) \approx Y(s,x) = a(s)x + b(s)x^2 \quad (1).$$

In the equation (1), a(s) and b(s) are used as coefficient a and coefficient b in a sense that both coefficient a and coefficient b depend on incident light intensity s. Coefficient a(s) of the linear term indicates an inclination of the ideal straight line, and coefficient b(s) of the quadratic term indicates the degree of deviation from the ideal straight line.

The following is a result of evaluation of a degree to which quadratic term $b(s)x^2$ (non-linear term) indicating the degree of deviation from the ideal straight line is with respect to linear term a(s)x reflecting the ideal straight line. A ratio of the quadratic term to the linear term (ratio of deviation from the ideal straight line) can be expressed as follows:

$$b(s)x^2/a(s)x = b(s)x/a.$$

For each of the combinations of the incident light intensities (0.1 to 0.9) and the exposure times (10 to 100 ms), the ratio of deviation from the ideal straight line is shown as follows.

| Incident light intensity | Exposure time [ms] | | | | | | | | | |
|---|---|---|---|---|---|---|---|---|---|---|
| | 10 | 20 | 30 | 40 | 50 | 60 | 70 | 80 | 90 | 100 |
| 0.1 | 0.5% | 1.0% | 1.5% | 2.0% | 2.5% | 3.0% | 3.5% | 4.0% | 4.5% | 5.0% |
| 0.2 | 0.5% | 0.9% | 1.4% | 1.9% | 2.4% | 2.8% | 3.3% | 3.8% | 4.3% | 4.7% |
| 0.3 | 0.4% | 0.8% | 1.3% | 1.7% | 2.1% | 2.5% | 3.0% | 3.4% | 3.8% | 4.2% |
| 0.4 | 0.4% | 0.8% | 1.2% | 1.6% | 2.0% | 2.4% | 2.8% | 3.2% | 3.6% | 3.9% |
| 0.5 | 0.4% | 0.7% | 1.1% | 1.5% | 1.8% | 2.2% | 2.6% | 2.9% | 3.3% | 3.7% |
| 0.6 | 0.4% | 0.7% | 1.1% | 1.5% | 1.8% | 2.2% | 2.6% | 2.9% | 3.3% | 3.7% |
| 0.7 | 0.4% | 0.7% | 1.1% | 1.4% | 1.8% | 2.1% | 2.5% | 2.9% | 3.2% | 3.6% |
| 0.8 | 0.3% | 0.6% | 0.9% | 1.3% | 1.6% | 1.9% | 2.2% | 2.5% | 2.8% | 3.1% |
| 0.9 | 0.3% | 0.6% | 0.9% | 1.2% | 1.5% | 1.8% | 2.1% | 2.4% | 2.7% | 3.0% |

The table above shows that when the exposure time is 10 [ms], the ratio of deviation from the ideal straight line can be reduced to be lower than 1% for all incident light intensities. However, when the exposure time is equal to or longer than 20 [ms], the ratio of deviation is not lower than 1% for some incident light intensities. It can also be seen that at the same exposure time, as the incident light intensity becomes lower, the ratio of deviation from the ideal straight line becomes higher.

The measurement result described above shows that various coefficients used in the process of correcting the output linearity also needs to be determined in consideration of the incident light intensity.

Referring to FIG. 6B, it can be seen that when the exposure time is 10 to 100 [ms], the light reception sensitivity ratio decreases with increase in exposure time for all incident light intensities. It can also be seen that the degree of decrease in light reception sensitivity ratio varies depending on the incident light intensity.

Referring again to FIG. 4, according to the measurement result described above, the output linearity is maintained when the exposure time is shorter than standard exposure time ts [ms] (e.g., 10 [ms]), and this range can be regarded as "linear range". Namely, the range of the exposure time in which the output value from detector 120 is proportional to the intensity of the light incident on detector 120 corresponds to "linear range".

In contrast, the output linearity is not maintained when the exposure time is longer than standard exposure time ts [ms], and this range can be regarded as "non-linear range". Namely, the range of the exposure time in which the output value from detector 120 is not proportional to the intensity of the light incident on detector 120 corresponds to "non-linear range".

For the sake of convenience in description, FIG. 4 shows the example in which the linear range and the non-linear range are arranged with standard exposure time ts being a boundary. However, a range not belonging to either the linear range or the non-linear range may be arranged between these two ranges.

In the method for correcting the output linearity according to the present embodiment, the output signal obtained in the non-linear range is corrected with respect to the output linearity appearing in the linear range.

(b3: Process of Correcting Output Linearity)

Referring again to FIG. 4, in the method for correcting the output linearity according to the present embodiment, quadratic term $bx^2$ for exposure time x is subtracted from actual Sig-Dark value y obtained at certain exposure time x, to determine ideal Sig-Dark value y'. Coefficient b of the quadratic term can be calculated using a correction coefficient $\alpha$ and a correction coefficient $\beta$, as described below. Namely, in the process of correcting the output linearity according to the present embodiment, a correction equation indicated by the following equation (2) is used:

$$y' = y - bx^2 \quad (2)$$

$$= y - \left\{ \alpha \left( \frac{-(\beta x + 1) + \sqrt{(\beta x + 1)^2 + 4\alpha y}}{2\alpha x} \right)^2 + \beta \left( \frac{-(\beta x + 1) + \sqrt{(\beta x + 1)^2 + 4\alpha y}}{2\alpha x} \right)^2 \right\} x^2.$$

Figure 7:
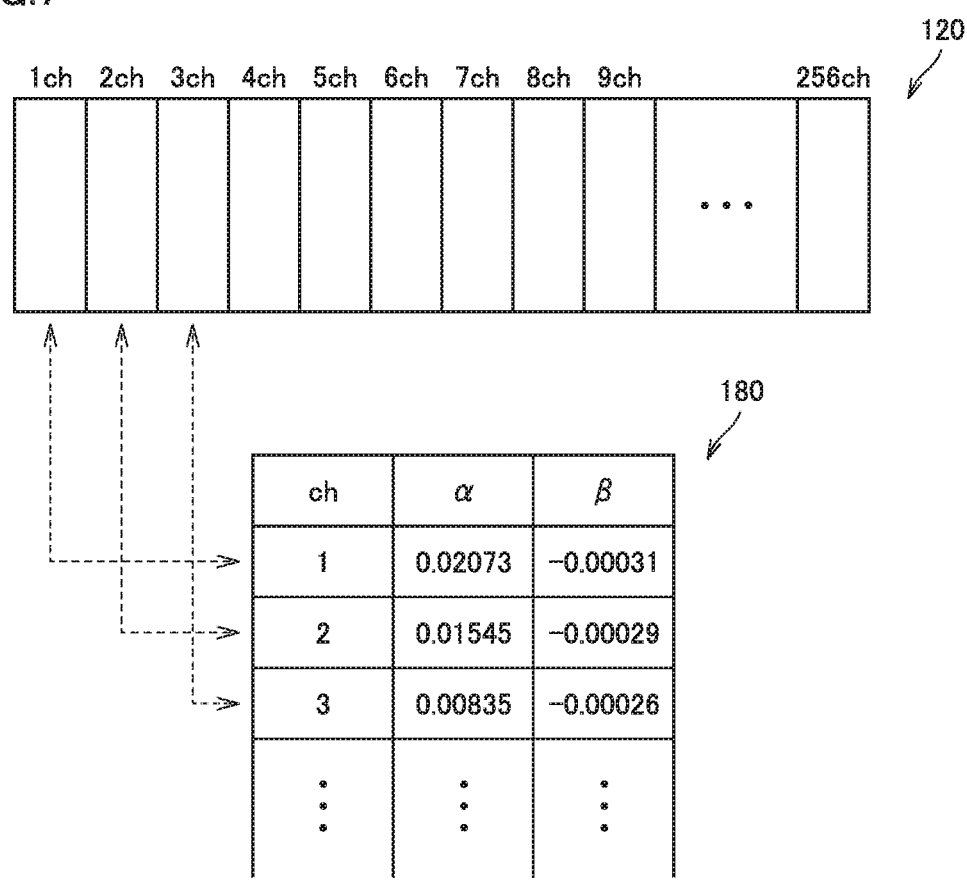
FIG. 7 is a schematic diagram for describing coefficient data related to the process of correcting the output linearity in the optical measurement apparatus according to the present embodiment.

Coefficient data related to the process of correcting the output linearity in optical measurement apparatus 100 according to the present embodiment will be described with reference to FIG. 7. Optical measurement apparatus 100 is configured to be able to perform spectroscopic measurement, and a plurality of detection surfaces (InGaAs photodiodes) are prepared as detector 120. For example, when 256 channels are available, a correction coefficient table 180 including a set of correction coefficients $\alpha$ and $\beta$ is preliminarily prepared for each channel. In this way, correction coefficients $\alpha$ and $\beta$ are determined for each channel. Controller 130 can refer to correction coefficient table 180. A method for obtaining correction coefficient table 180 will be described below.

Figure 8:
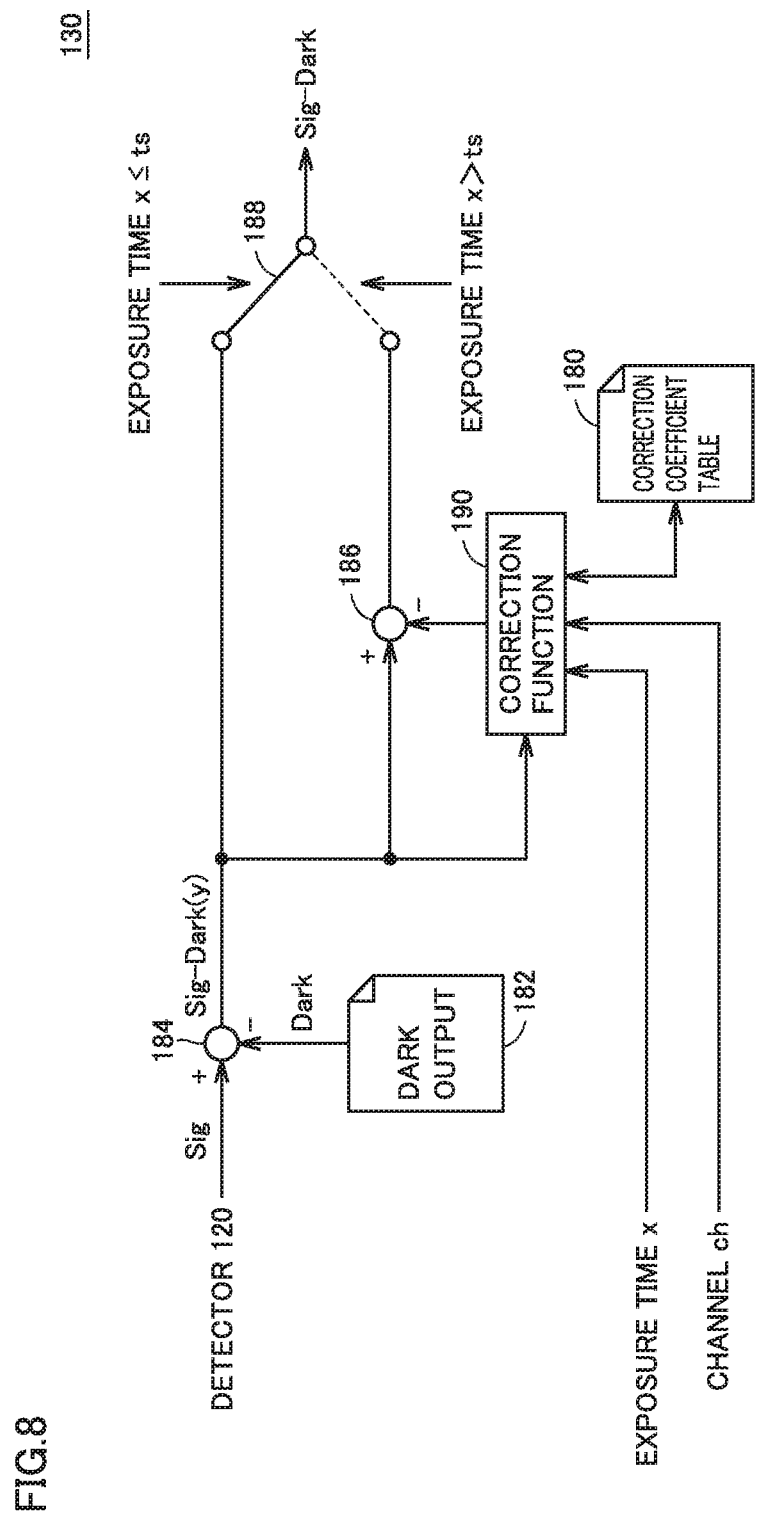
FIG. 8 is a schematic diagram for describing the process of correcting the output linearity in the optical measurement apparatus according to the present embodiment.

The process of correcting the output linearity in optical measurement apparatus 100 according to the present embodiment will be described with reference to FIG. 8. The functional blocks shown in FIG. 8 are typically mounted in controller 130 of optical measurement apparatus 100.

Controller 130 obtains an output value by measuring a light sample at any exposure time with detector 120. Suppose the operation of detecting the incident light incident on detector 120 is performed at any exposure time x [ms]. Dark correction is first made to an output signal (Sig) output from any channel of detector 120. Specifically, the process of subtracting a preliminarily obtained dark output (Dark) 182 from the output signal (Sig) is performed in a subtracter 184 to calculate a dark-corrected output value (Sig-Dark). This dark correction may be made in detector 120.

In accordance with whether or not exposure time x at which the detection operation in detector 120 is performed is not longer than standard exposure time ts, it is selected whether to output the dark-corrected output value (Sig-Dark) as it is or to output the corrected output value obtained by performing the above-described correction process. For example, this selection may be made using a switch 188 and the like switched in accordance with a difference between exposure time x and standard exposure time ts.

When the process of correcting the output linearity is performed, a correction function 190 for calculating the non-linear term shown in the equation (2) above is used. Actual Sig-Dark value y and exposure time x are input to correction function 190, and correction coefficient $\alpha$ and correction coefficient $\beta$ corresponding to the target channel are read from correction coefficient table 180 (see FIG. 7), to calculate a corrected value. Then, an amount of correction ($bx^2$) is subtracted from dark-corrected output value (Sig-Dark value) y in a subtracter 186 to calculate Sig-Dark value y'. This calculated Sig-Dark value y' is output to the outside as the corrected output value.

The amount of correction ($bx^2$) when exposure time x exceeds standard exposure time ts includes a product of coefficient b and a square of exposure time x. Coefficient b indicates a degree to which output value (Sig-Dark value) y obtained when the light sample is measured with detector 120 at the exposure time within the range exceeding standard exposure time ts (non-linear range) deviates from the output linearity (y'=ax) obtained when the light sample is measured with detector 120 at the exposure time within the range of not longer than standard exposure time ts (linear range).

Coefficient b itself also depends on output value (Sig-Dark value) y and exposure time x. Therefore, in the correction process according to the present embodiment, the output linearity is corrected using preliminarily obtained correction coefficients $\alpha$ and $\beta$, exposure time x at which the detection operation is performed, and dark-corrected output value (Sig-Dark value) y. In other words, as shown in the equation (2) above, coefficient b is determined based on dark-corrected output value (Sig-Dark value) y, exposure time x at which output value (Sig-Dark value) y is obtained, and predetermined correction coefficients α and β.

As shown in FIG. 8, when the exposure time at which output value (Sig-Dark value) y is obtained is within the predetermined range (not longer than standard exposure time ts), controller 130 outputs the output value as it is. On the other hand, when the exposure time at which output value (Sig-Dark value) y is obtained is not within the predetermined range (not longer than standard exposure time ts), controller 130 corrects the output value with the amount of correction and outputs the corrected output value. The amount of correction includes a value obtained by multiplying coefficient b with a square of exposure time x, and coefficient b is determined based on output value (Sig-Dark value) y, exposure time x at which output value (Sig-Dark value) y is obtained, and correction coefficients α and β.

(b4: Derivation of Correction Equation)

Next, derivation of the correction equation shown in the equation (2) above from the approximate equation shown in the equation (1) above will be described. The approximate equation shown in the equation (1) is again presented below:

$$Y(s,x)=a(s)x+b(s)x^2 \qquad (1).$$

In the equation above, coefficient a(s) is a coefficient of the linear term of the approximate equation, and coefficient b(s) is a coefficient of the quadratic term of the approximate equation. As shown in FIG. 4, the output linearity is ensured in the linear range, and thus, coefficient a(s) of the linear term in the equation (1) can be regarded as a result obtained by dividing output value ys at standard exposure time ts by standard exposure time ts (inclination in the linear range). In other words, the following relational equation is satisfied:

$$a(s) \approx ys/ts.$$

Then, the approximate equation shown in the equation (1) can be expressed like the following equation (3):

$$Y(s,x)=(ys/ts)x+b(s)x^2 \text{ (where } x>ts) \qquad (3).$$

Next, coefficient b(s) of the quadratic term can be calculated using regression analysis (typically, a least square method) described below.

First, in order to calculate coefficient $b(s_j)$ at incident light intensity $s=s_j$, incident light intensity s is kept constant $(s=s_j)$ and the exposure time is varied in N stages (x: $x_1$ to $x_N$), to obtain each Sig-Dark value.

Assuming that $S_j$ represents a summation, for all exposure times ($x_1$ to $x_N$), of a square of a difference between a value of approximate equation $Y(s_j, x_k)$ and actual Sig-Dark value $y(s_j, x_k)$ at incident light intensity $s_j$ and exposure time $x_k$, $S_j$ can be expressed like the following equation (4). Furthermore, a value of $b=b(s_j)$ that minimizes $S_j$ shown in the equation (4) is provided in accordance with the limiting condition of $\partial S_j/\partial b=0$, and thus, the value of $b=b(s_j)$ can be determined like the following equation (5).

$$S_j = \sum_{k=1}^{N} \{y(s_j, x_k) - (a(s_j)x_k + b(s_j)x_k^2)\}^2 \qquad (4)$$

$$b(s_j) = \frac{\sum_{k=1}^{N} x_k^2 y(s_j, x_k) - a(s_j)\sum_{k=1}^{N} x_k^3}{\sum_{k=1}^{N} x_k^4} \qquad (5)$$

As described above, coefficient $b(s_j)$ of the quadratic term at certain incident light intensity $s_j$ is calculated.

Similarly to the above-described procedure, incident light intensity $s_j$ is varied in M stages and coefficient $b(s_j)$ of the quadratic term at each incident light intensity (s: $s_1$ to $S_M$) is calculated based on each output Sig-Dark value. The variation of incident light intensity $s_j$ is preferably selected such that the Sig-Dark value appears over the entire output range. However, it is not necessary to strictly equalize the variation width of incident light intensity $s_j$ and the like, and adjustment may be made as appropriate so as to prevent concentration on the vicinity of a certain intensity.

As described above, coefficient b(s) of the quadratic term included in approximate equation $Y(s_j, x_k)$ depends on incident light intensity $s_j$. Thus, coefficient b(s) of the quadratic term is determined using the correlation with coefficient a(s) of the linear term that forms approximate equation Y(s, x) shown in the equation (1).

Specifically, an approximate equation B(s) showing a relation between coefficient a(s) of the linear term and coefficient b(s) of the quadratic term as shown in the following equation (6) is introduced:

$$b(s) \approx B(s) = \alpha a(s)^2 + \beta a(s) = \alpha(ys_j/ts)^2 + \beta(ys_j/ts) \qquad (6).$$

In the equation (6), coefficient a(s) is set at $a(s) \approx ys_j/ts$. $ys_j$ indicates a Sig-Dark value obtained when the light sample is measured at incident light intensity $s_j$ and standard exposure time ts. The value of coefficient a(s) of the linear term is determined based on the premise that the proportional relation between standard exposure time ts and the Sig-Dark value should be maintained for each incident light intensity even when the exposure time is increased. Since the output linearity appearing in the linear range may only be used, the value of coefficient a(s) may be determined using any exposure time within the linear range and a Sig-Dark value corresponding thereto. However, the use of the Sig-Dark value at the longest exposure time within the linear range makes it possible to reduce an error included in the obtained output linearity.

Figure 9:
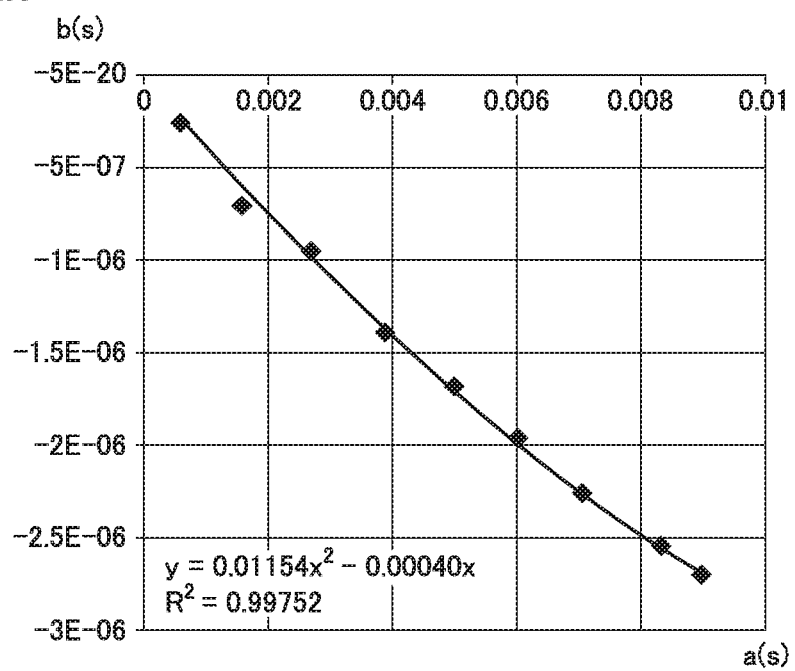
FIG. 9 is a diagram showing one example of a correspondence relation between a coefficient a(s) of a linear term and a coefficient b(s) of a quadratic term obtained from the measurement results of the InGaAs linear image sensor.

FIG. 9 shows one example of the correspondence relation between coefficient a(s) of the linear term and coefficient b(s) of the quadratic term obtained from the measurement result of the InGaAs linear image sensor. As shown in FIG. 9, it can be seen that coefficient b(s) of the quadratic term can be estimated with a high degree of accuracy in accordance with a regression equation (in the form of a quadratic equation) for coefficient a(s) of the linear term.

Since correction coefficient α and correction coefficient β are constant values unique to the element forming detector 120, the above-described relation is used to determine correction coefficient α and correction coefficient β by regression analysis (typically, the least square method). At this time, regression analysis is performed while coefficient a(s) of the linear term is fixed as a value by using Sig-Dark value $ys_j$ from detector 120 at the exposure time (typically, standard exposure time ts) within the linear range, which is used to determine an approximate equation $Y(s_j, x_k)$ corresponding to the linear range.

Assuming that T represents a summation, for all incident light intensities $s_j$, of a difference between coefficient $b(s_j)$ of the quadratic term calculated in accordance with the above-described procedure and the value of corresponding approximate equation $B(s_j)$, T can be expressed like the following equation (7):

$$T = \Sigma[b(s_j) - \{\alpha(ys_j/ts)^2 + \beta(ys_j/ts)\}]^2 \quad (7).$$

In accordance with the limiting condition that minimizes T, i.e., $\partial T/\partial \alpha = 0$ and $\partial T/\partial \beta = 0$, a simultaneous equation for $(\alpha, \beta)$ shown in the following equation (8) can be obtained. The simultaneous equation (8) is solved for $(\alpha, \beta)$ to obtain the equation (9).

$$\begin{pmatrix} \sum_{j=1}^{M}\left(\frac{ys_j}{ts}\right)^4 & \sum_{j=1}^{M}\left(\frac{ys_j}{ts}\right)^3 \\ \sum_{j=1}^{M}\left(\frac{ys_j}{ts}\right)^3 & \sum_{j=1}^{M}\left(\frac{ys_j}{ts}\right)^2 \end{pmatrix} \begin{pmatrix} \alpha \\ \beta \end{pmatrix} = \begin{pmatrix} \sum_{j=1}^{M}\left(\frac{ys_j}{ts}\right)^2 b(s_j) \\ \sum_{j=1}^{M}\left(\frac{ys_j}{ts}\right) b(s_j) \end{pmatrix} \quad (8)$$

$$\begin{pmatrix} \alpha \\ \beta \end{pmatrix} = \begin{pmatrix} \sum_{j=1}^{M}\left(\frac{ys_j}{ts}\right)^4 & \sum_{j=1}^{M}\left(\frac{ys_j}{ts}\right)^3 \\ \sum_{j=1}^{M}\left(\frac{ys_j}{ts}\right)^3 & \sum_{j=1}^{M}\left(\frac{ys_j}{ts}\right)^2 \end{pmatrix}^{-1} \begin{pmatrix} \sum_{j=1}^{M}\left(\frac{ys_j}{ts}\right)^2 b(s_j) \\ \sum_{j=1}^{M}\left(\frac{ys_j}{ts}\right) b(s_j) \end{pmatrix} \quad (9)$$

As described above, approximate equation B(s) for coefficient b(s) can be determined. The equation (6) indicating determined approximate equation B(s) for coefficient b(s) is substituted into the equation (4). Then, approximate equation Y(s, x) indicating actual Sig-Dark value y from detector 120 at the incident light intensity and the exposure time can be calculated as shown in the following equation (10):

$$y \approx Y(s, x) \quad (10)$$
$$= (ys/ts)x + \{\alpha(ys/ts)^2 + \beta(ys/ts)\}x^2.$$

Since Sig-Dark value y'=y'(s, x) subjected to the process of correcting the output linearity is obtained simply by subtracting a portion corresponding to the non-linear term from approximate equation Y(s, x) shown in the equation (10), Sig-Dark value y'=y'(s, x) subjected to the process of correcting the output linearity can be expressed like the following equation (11), using actual Sig-Dark value y:

$$y' \approx y - \{\alpha(ys/ts)^2 + \beta(ys/ts)\}x^2 \quad (11)$$

Since corrected Sig-Dark value y' shown in the equation (11) should be located on ideal straight line y=(ys/ts)x, the value of coefficient a (=ys/ts) of the linear term can be determined as shown in the following equation (12), by regarding the equation (10) as a quadratic equation of (ys/ts) and solving the equation (10):

$$\left(\frac{ys}{ts}\right) \cong \frac{-(\beta x + 1) + \sqrt{(\beta x + 1)^2 + 4\alpha y}}{2\alpha x}. \quad (12)$$

The equation (12) is substituted into the equation (11). Then, the correction equation shown in the equation (2) above can be finally derived.

As described above, in order to determine correction coefficients $\alpha$ and $\beta$ and the correction equation shown in the equation (2) above, measurement of a plurality of output values (Sig-Dark values) in the linear range is not required, and what is required is measurement at only one exposure time at which the output linearity in the linear range at the target incident light intensity can be specified. Therefore, the time and effort for obtaining correction coefficients $\alpha$ and $\beta$ can be reduced.

In addition, coefficient b included in the correction equation depends on both output value (Sig-Dark value) y and exposure time x, and ideal Sig-Dark value (corrected Sig-Dark value) y' can be normally determined only after the parameters of output value (Sig-Dark value) y and exposure time x are both set. In contrast, in the present embodiment, the output linearity estimated using the measured value in the linear range is used and the correction equation not requiring input of the parameters is used, and thus, the amount of correction can be immediately calculated for each measurement.

(b5: Method for Determining Linear Range and Non-linear Range)

The linear range and the non-linear range shown in FIG. 4 are preliminarily obtained. The linear range which is the range of the exposure time in which the output linearity is maintained depends on the device properties of detector 120. Thus, by varying each of the incident light intensity and the exposure time and obtaining the Sig-Dark values, and performing regression analysis using the linear equation for each incident light intensity, the range in which the amount of deviation from the ideal straight line is not greater than a permissible value may be determined as the linear range.

As to this permissible value, the amount of deviation from the ideal straight line may be set to be not greater than 1%, with reference to the determination criterion about response linearity of a spectrophotometer described in the JIS standards (JIS Z8724 (method for measuring a light source color)), for example.

By the above-described preliminary measurement, the linear range, i.e., the standard exposure time is preliminarily determined.

Of the settable range of the exposure time, the range from the shortest exposure time to the standard exposure time does not necessarily correspond to the linear range. Specifically, although the foregoing description has illustrated by way of example the case in which maintenance of the output linearity becomes impossible with increase in exposure time, maintenance of the output linearity may in some cases become impossible with decrease in exposure time. In such a case, of the settable range of the exposure time for detector 120, any range of the exposure time in which the output linearity can be maintained may be set as the linear range, and the correction method according to the present embodiment may be applied to a range other than this linear range.

(b6: Obtainment of Correction Coefficient Table)

Next, the method for obtaining correction coefficient table 180 shown in FIG. 7 will be described. The process of obtaining correction coefficient table 180 may be performed by controller 130 of optical measurement apparatus 100, or may be performed by using processing apparatus 200 connected to optical measurement apparatus 100 as a calibration apparatus. Typically, the process of obtaining correction coefficient table 180 is performed as a part of the calibration work before shipment of optical measurement apparatus 100. By way of example, description will be given below of the case in which an engineer of a manufacturer performs a prescribed operation using optical measurement apparatus 100 and a light source for calibration, and processor 202 of processing apparatus 200 executes calibration program 209 (see FIG. 2), to obtain correction coefficient table 180.

Figure 10:
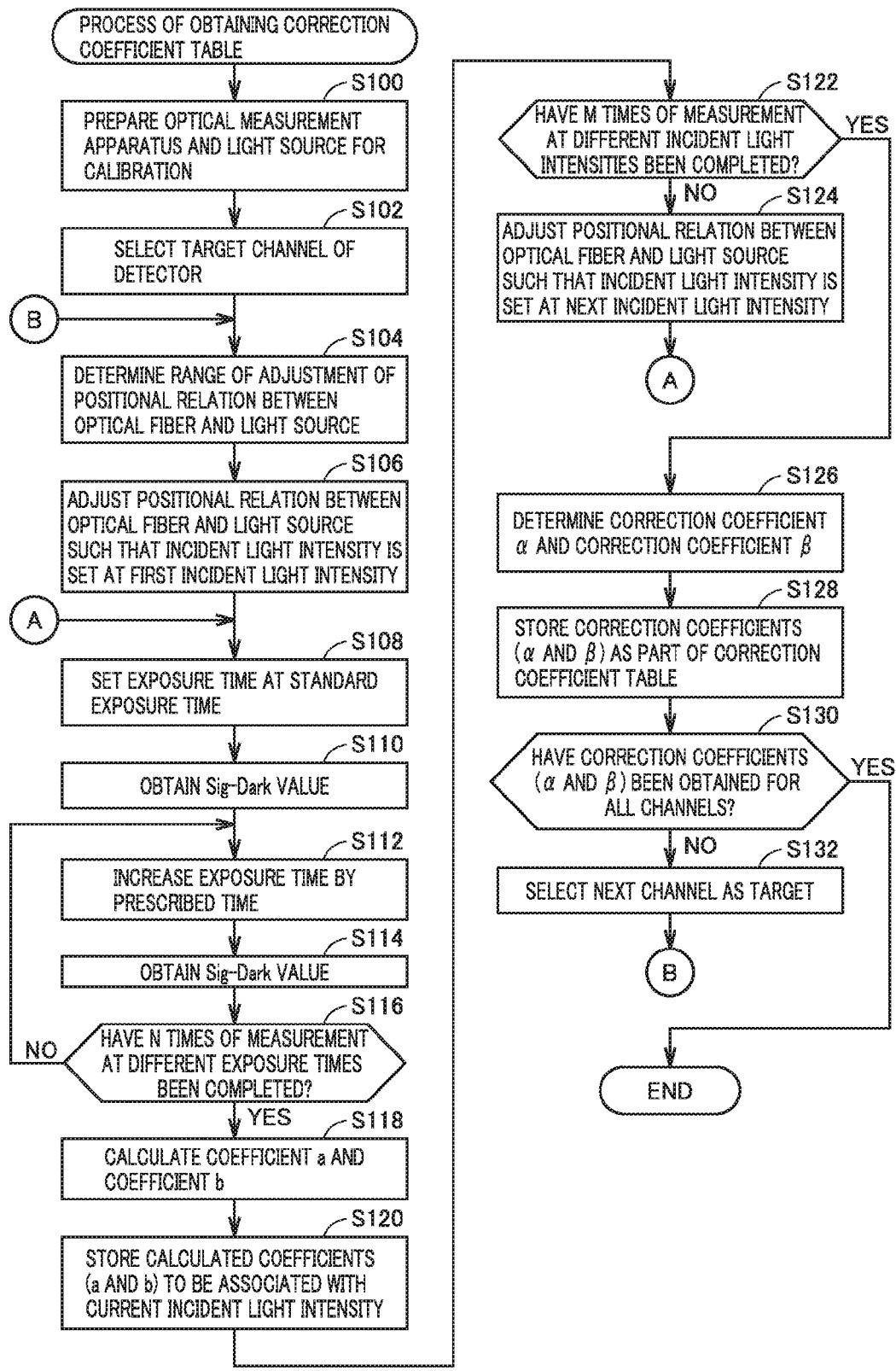
FIG. 10 is a flowchart showing a process procedure of a method for obtaining a correction coefficient table stored in the optical measurement apparatus according to the present embodiment.

FIG. 10 shows a process procedure of the method for obtaining correction coefficient table 180 stored in optical measurement apparatus 100 according to the present embodiment. Referring to FIG. 10, optical measurement apparatus 100 and the light source for calibration are prepared (step S100).

First, a target channel is selected from the plurality of channels owned by detector 120 (step S102). Then, a range of adjustment of the positional relation between optical fiber 2 and the light source emitting the light sample is determined such that the incident light intensity detected in optical measurement apparatus 100 can be varied in M stages (step S104). Then, the positional relation between optical fiber 2 and the light source emitting the light sample is adjusted such that the incident light intensity detected in optical measurement apparatus 100 is set at the first incident light intensity of the M-stage incident light intensities (step S106).

Next, output values (Sig-Dark values) when the light sample is measured at the N-stage exposure times including standard exposure time ts are obtained. In other words, the process of obtaining output values by measuring a light sample having a prescribed light intensity at a plurality of exposure times with detector 120 is performed. The obtained output values include output values obtained by measuring the light sample with detector 120 at a plurality of exposure times including an exposure time within the linear range (typically, standard exposure time ts) and a plurality of exposure times within the non-linear range.

Specifically, the exposure time is set at standard exposure time ts (step S108), and the measurement operation is performed to obtain an output value (Sig-Dark value) (step S110). Next, the exposure time is increased from the current value by the prescribed time (step S112), and the measurement operation is performed to obtain an output value (Sig-Dark value) (step S114). Then, it is determined whether or not the N times of measurement at different exposure times have been completed (step S116). When the N times of measurement have not been completed (NO in step S116), the process in step S112 and the subsequent steps is repeated.

When the N times of measurement have been completed (YES in step S116), the process of determining a set of coefficients that define an approximate equation for the output values is performed.

Specifically, processing apparatus 200 calculates coefficient a of the linear term in the equation (1) above from the output value at standard exposure time ts, and calculates coefficient b of the quadratic term by regression analysis (typically, the least square method; refer to the equations (4) and (5) above) of the plurality of output values obtained for the respective exposure times (step S118). Then, the calculated coefficients (a and b) are stored to be associated with the current incident light intensity (step S120).

It is determined whether or not the M times of measurement at different incident light intensities have been completed (step S122). When the M times of measurement have not been completed (NO in step S122), the intensity of the light incident on detector 120 is varied, and the process of obtaining the output values and the process of determining the set of coefficients are repeated. Specifically, the positional relation between optical fiber 2 and the light source emitting the light sample is adjusted such that the incident light intensity detected in optical measurement apparatus 100 is set at the next incident light intensity of the M-stage incident light intensities (step S124). Then, the process in step S108 and the subsequent steps is repeated.

When the M times of measurement have been completed (YES in step S122), the process of determining correction coefficients α and β by regression analysis of the coefficients (a and b) obtained for the respective light intensities is performed.

Specifically, processing apparatus 200 determines correction coefficient α and correction coefficient β by regression analysis (refer to the equations (6) to (9) above) of the set of coefficients (a and b) associated with the respective incident light intensities (step S126). Then, processing apparatus 200 stores the calculated correction coefficients (α and β) as a part of correction coefficient table 180 to be associated with the current channel (step S128).

It is determined whether or not the correction coefficients (α and β) have been obtained for all of the plurality of channels owned by detector 120 (step S130). When there remains a channel for which the correction coefficients (α and β) have not been obtained, of the plurality of channels owned by detector 120 (NO in step S130), the next channel of the plurality of channels owned by detector 120 is selected as a target (step S132). Then, the process in step S104 and the subsequent steps is repeated.

When the correction coefficients (α and β) have been obtained for all of the plurality of channels owned by detector 120 (YES in step S130), the process of obtaining correction coefficient table 180 ends.

(b7: Measurement Process)

Next, the process of measuring optical characteristics using optical measurement apparatus 100 according to the present embodiment will be described. FIG. 11 shows a process procedure of the measurement method using optical measurement apparatus 100 according to the present embodiment. Each step shown in FIG. 11 is performed mainly by controller 130 of optical measurement apparatus 100. Each step performed by controller 130 may be implemented by execution of the program by processor 132 of controller 130.

Referring to FIG. 11, controller 130 obtains set values related to the measurement process (step S200). The set values include the exposure time, the wavelength range, the number of times of measurement and the like. The light sample is input to spectroscopic measurement unit 110 through optical fiber 2.

Controller 130 determines whether or not the start of measurement has been triggered (step S202). When the start of measurement has been triggered (YES in step S202), controller 130 obtains an output value by measuring a light sample at any exposure time with detector 120. More specifically, controller 130 activates detector 120, selects the first channel of detector 120 of spectroscopic measurement unit 110 (step S204), and obtains an output value from the selected channel (step S206).

Controller 130 determines whether or not the currently set exposure time exceeds standard exposure time ts (step S208). When the currently set exposure time does not exceed standard exposure time ts (NO in step S208), the process in steps S210 to S212 is skipped.

When the currently set exposure time exceeds standard exposure time ts (YES in step S208), controller 130 refers to correction coefficient table 180 and reads correction coefficient α and correction coefficient β corresponding to the selected channel (step S210), and corrects the obtained output value (Sig-Dark value) using read correction coefficients α and β, the exposure time and the obtained output value (Sig-Dark value) (step S212). Namely, when the exposure time at which the output value is obtained is within the range exceeding standard exposure time ts (non-linear range), controller 130 corrects the output value with the amount of correction corresponding to the output value.

Then, controller 130 stores the output value obtained in step S206 or the output value corrected in step S212 to be associated with the selected channel (step S214).

Controller 130 determines whether or not the process has been completed for all channels of detector 120 (step S216). When there remains a channel for which the process has not been completed (NO in step S216), controller 130 selects the next channel of detector 120 of spectroscopic measurement unit 110 (step S218) and repeats the process in step S206 and the subsequent steps.

When the process has been completed for all channels (YES in step S216), controller 130 collectively outputs, as spectrums, the output values stored to be associated with the respective channels (step S220). Then, controller 130 determines whether or not the currently set number of times of measurement has been completed (step S222).

When the currently set number of times of measurement has not been completed (NO in step S222), the process in step S204 and the subsequent steps is repeated. When the currently set number of times of measurement has been completed (YES in step S222), the measurement process ends.

<C. Improvement Effect>

Next, one example of an improvement effect produced by the method for correcting the output linearity according to the present embodiment will be described.

Figure 12A:
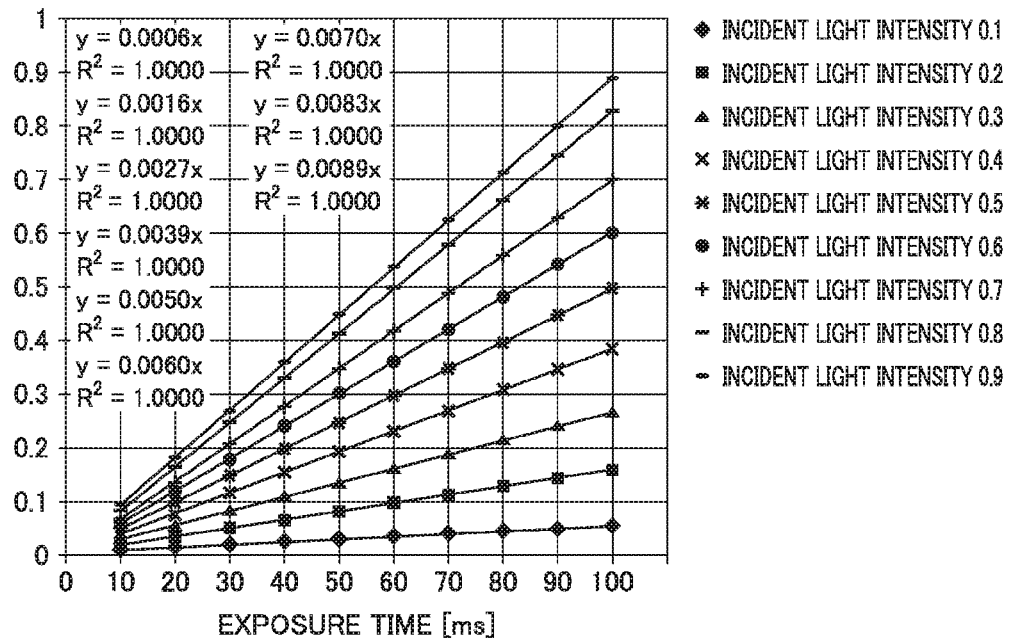
FIGS. 12A and 12B are diagrams showing one example of results of correction made to the measurement results shown in FIGS. 6A and 6B.
Figure 12B:
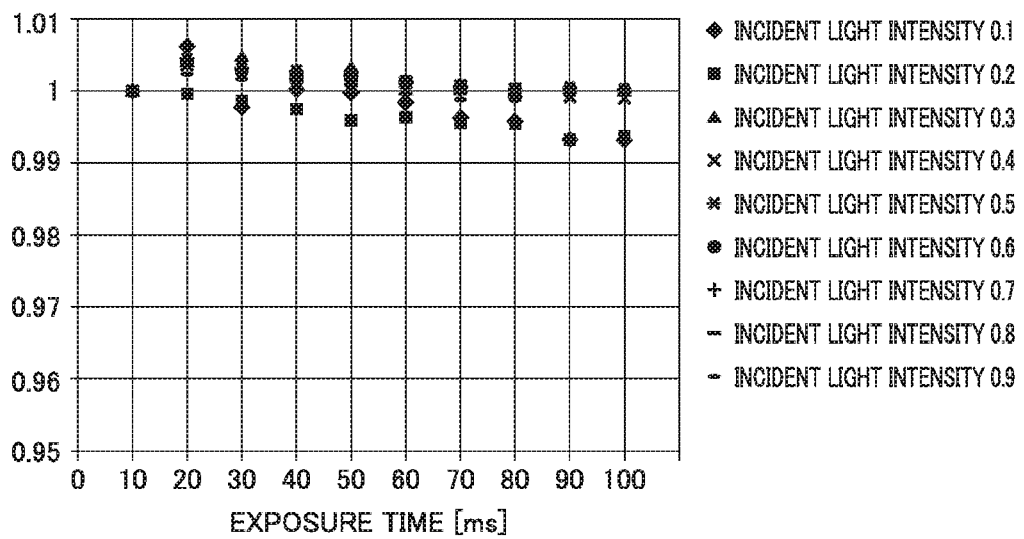

FIGS. 12A and 12B show one example of results of correction made to the measurement results shown in FIGS. 6A and 6B. Referring to FIG. 12A, the regression equation in the form of the linear equation (y=ax+b) for corrected Sig-Dark value y' is obtained for all incident light intensities, and determination coefficient $R^2$ is 1. As described above, it can be seen that even when the exposure time exceeds standard exposure time is (10 [ms] in this example), the output linearity is sufficiently maintained.

Referring to FIG. 12B, it can be seen that, by applying the method for correcting the output linearity according to the present embodiment, the light reception sensitivity ratio falls within the range of 0.99 to 1.01 (i.e., the deviation from the ideal straight line is within ±1%) for all incident light intensities and thus the excellent output linearity is obtained. Particularly, as compared with the measurement result of the light reception sensitivity ratio before correction as shown in FIG. 6B, the significant improvement effect can be understood.

Optical measurement apparatus 100 according to the present embodiment can perform spectroscopic measurement. As described above, the process of correcting the output linearity is performed on each channel of the InGaAs linear image sensor forming detector 120. As a result, the measurement result is output as a spectrum with improved output linearity for each wavelength component. One example of an improvement effect about such spectrum output as the measurement result will be shown.

Figure 13A:
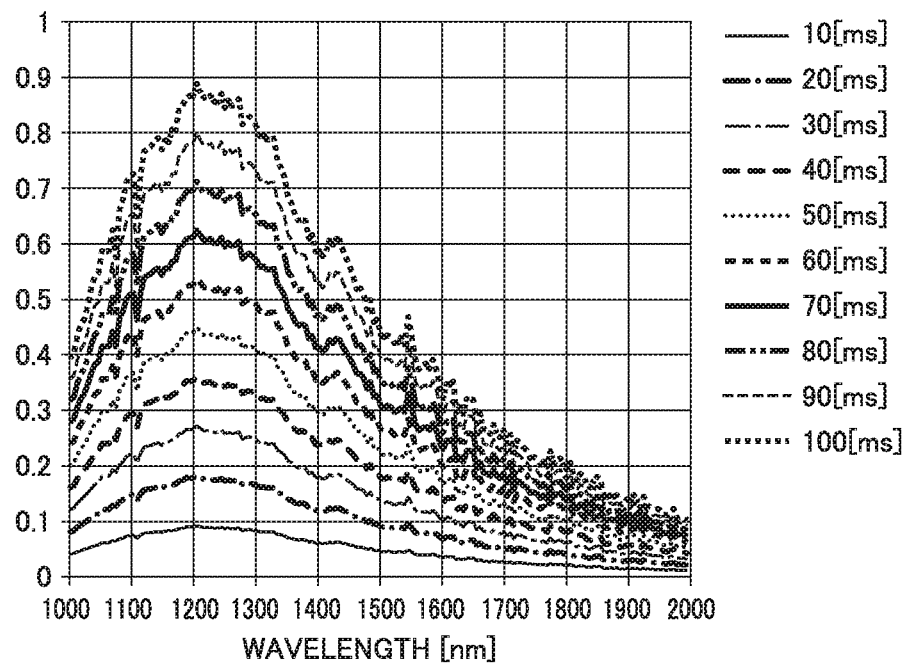
FIGS. 13A and 13B are diagrams showing one example of results of measurement of light sample from a light source using the optical measurement apparatus according to the present embodiment.
Figure 13B:
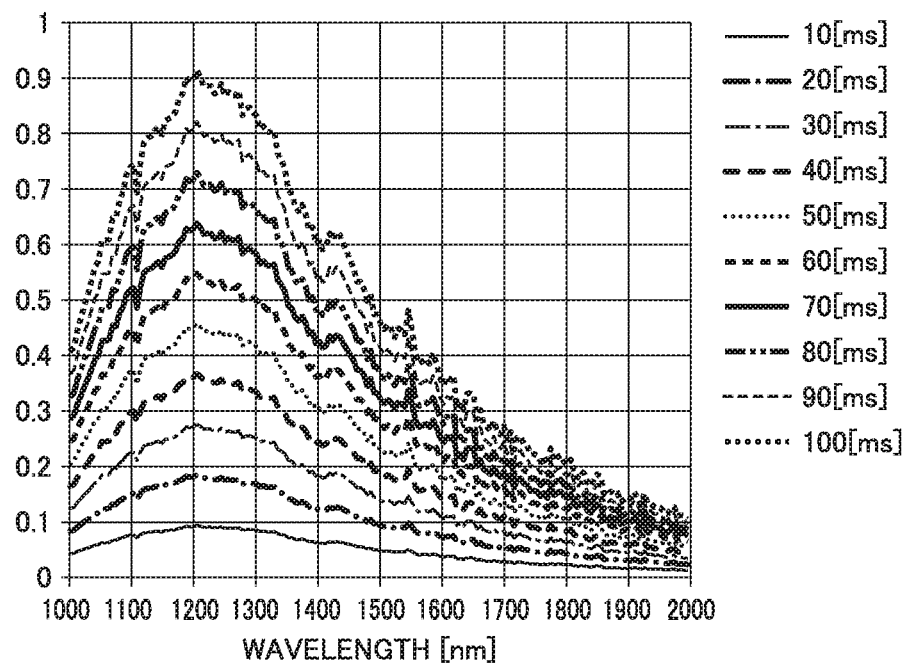
Figure 14A:
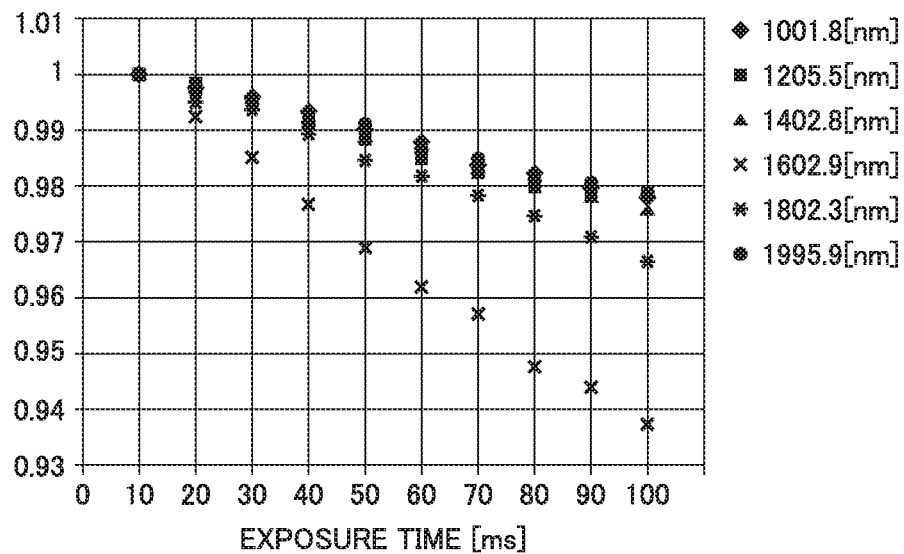
FIGS. 14A and 14B are diagrams showing results of evaluation of a light reception sensitivity ratio for each spectrum shown in FIGS. 13A and 13B.
Figure 14B:
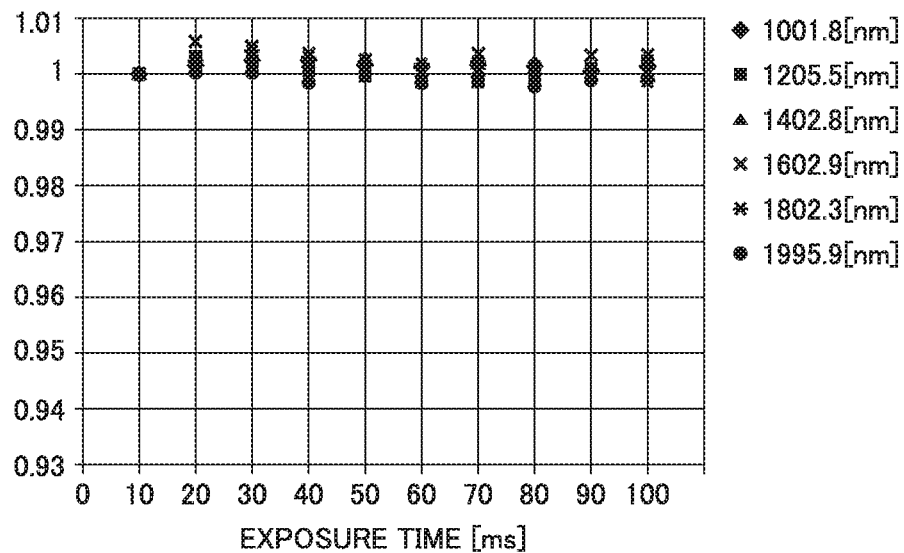

FIGS. 13A and 13B show one example of results of measurement of the light sample from the light source using optical measurement apparatus 100 according to the present embodiment. FIGS. 14A and 14B show results of evaluation of the light reception sensitivity ratio for each spectrum shown in FIGS. 13A and 13B. FIGS. 13A, 13B, 14A, and 14B show measurement results obtained by using the light emitted from a halogen light source as a light sample source and measuring a spectrum in the wavelength range of 1000 to 2000 [nm]. The exposure time was varied within the range of 10 to 100 [ms] and a spectrum at each exposure time was measured.

FIG. 13A shows a spectrum before performing the process of correcting the linearity according to the present embodiment, and FIG. 13B shows a spectrum after performing the process of correcting the linearity according to the present embodiment. Comparing FIG. 13A with FIG. 13B, the spectrum when the longer exposure time is set can be particularly measured more accurately.

FIG. 14A shows a light reception sensitivity ratio corresponding to the spectrum for each exposure time shown in FIG. 13A, and FIG. 14B shows a light reception sensitivity ratio corresponding to the spectrum for each exposure time shown in FIG. 13B. According to the distribution of the light reception sensitivity ratio shown in FIG. 14A, the degree of degradation in light reception sensitivity ratio is serious particularly for the wavelength component of 1602.9 [nm]. In contrast, according to the properties of the light reception sensitivity ratio after correction as shown in FIG. 14B, it can be seen that the light reception sensitivity ratio falls within the range of 0.99 to 1.01 (i.e., the deviation from the ideal straight line is within ±1%) for all wavelength components and thus the excellent output linearity is obtained.

As described above, it can be seen that the use of the method for correcting the output linearity according to the present embodiment makes it possible to maintain the excellent output linearity without depending on the magnitude of the exposure time and the magnitude of the incident light intensity.

<D. Modification>

Although the description has been given above of the example in which the common correction equation is applied to the Sig-Dark value obtained in the non-linear range, different correction equations may be applied depending on the range of the exposure time. For example, when regression of the Sig-Dark value can be performed in accordance with a quadratic equation for the exposure time in a range of the relatively short exposure time in the non-linear range, and regression of the Sig-Dark value can be performed in accordance with a cubic equation for the exposure time in a range of the relatively long exposure time in the non-linear range, correction equations corresponding to the quadratic equation and the cubic equation may be used.

Although the description has been given above of the example in which the non-linear range is set on the side where the exposure time is longer than the exposure time in the linear range, the non-linear range may in some cases be set on the side where the exposure time is shorter than the exposure time in the linear range. In this case as well, the process of correcting the output linearity according to the present embodiment may be applied similarly to the foregoing description.

Although the description has been given above of the example in which the present invention is applied to optical measurement in the near-infrared region, the present invention is not limited to the near-infrared region and is also applicable to the other wavelength regions. For example, the present invention is also applicable to the case of using a sensor made of Si, Ge or the like and having a sensitivity to the visible light region.

<E. Advantage>

According to the present embodiment, degradation in output linearity due to variation of the exposure time, which occurs in the detector (e.g., the InGaAs linear image sensor) having a detection sensitivity to at least the near-infrared region, can be corrected at the time of measurement. In the optical measurement method according to the present embodiment, by preliminarily obtaining correction coefficients α and β, the amount of correction can be uniquely determined based on the output value (Sig-Dark value) and the exposure time at the time of measurement. Namely, the amount of correction reflecting both the incident light intensity and the exposure time at the time of measurement can be easily determined based on preliminarily obtained correction coefficients α and β. Therefore, a reference device or the like for correcting the output linearity is not required, and thus, the apparatus configuration can be simplified and the process time required for correction of the output linearity can be reduced to substantially zero.

In the optical measurement method according to the present embodiment, correction coefficients α and β unique to each channel included in the detector are obtained. Therefore, even when there is variability or the like of the element forming the detector, the output linearity can be corrected appropriately. In addition, correction coefficients α and β are determined by regression analysis, and thus, the number of times of preliminary measurement required to determine correction coefficients α and β may be not so large. Therefore, the process of preliminarily obtaining correction coefficients α and β can be simplified.

The other advantages of the optical measurement apparatus and the optical measurement method according to the present embodiment will become more apparent from the foregoing description.

While the embodiment of the present invention has been described, it should be understood that the embodiment disclosed herein is illustrative and not limitative in any respect. The scope of the present invention is defined by the terms of the claims, and is intended to include any modifications within the scope and meaning equivalent to the terms of the claims.

REFERENCE SIGNS LIST 1 optical measurement system; 2 optical fiber; 100 optical measurement apparatus; 110 spectroscopic measurement unit; 112 connection unit; 114 optical slit; 116 shutter; 118 diffraction grating; 120 detector; 120a photodiode array; 120b read circuit; 122 cooling fin; 124 housing; 130 controller; 132, 202 processor; 132a correction process; 134 memory; 136 amplifier; 138 converter; 140 timing circuit; 142 drive circuit; 150 interface or interface circuit; 180 correction coefficient table; 184, 186 subtracter; 188 switch; 190 correction function; 200 processing apparatus; 204 main memory; 206 hard disk; 208 measurement program; 209 calibration program; 210 optical drive; 212 optical medium; 214 network interface; 216 display; 218 input unit; 220 bus; is standard exposure time.

What is claimed is:

1. An optical measurement method using a detector having a detection sensitivity to at least a near-infrared region, a first time range of exposure in which an output value from the detector is proportional to an intensity of light incident on the detector, and a second time range of exposure in which the output value from the detector is not proportional to the intensity of the light incident on the detector being obtained in advance, the optical measurement method comprising:

obtaining the output value by measuring a light sample with an exposure time length with the detector, the exposure time length including a first exposure time length within the first time range and a second exposure time length within the second time range;

correcting the output value with an amount of correction corresponding to the output value, when the second exposure time length with which the output value is obtained is within the second time range, the amount of correction comprising a product of a coefficient and a square of the second exposure time length, the coefficient indicating a degree to which the output value obtained when the light sample is measured with the detector with the second exposure time length within the second time range deviates from output linearity obtained when the light sample is measured with the detector at the first exposure time length within the first time range, the coefficient being determined based on the output value, the exposure time length with which the output value is obtained, and a correction coefficient, obtaining a plurality of output values by measuring a light sample having a prescribed light intensity at a plurality of exposure time lengths with the detector, the plurality of exposure time lengths comprising one first exposure time length within the first time range and a plurality of second exposure time lengths within the second time range;

determining a set of the coefficients that define an approximate equation for the obtained plurality of output values;

varying the intensity of the light incident on the detector, and repeating the step of obtaining the plurality of output values and the step of determining the set of the coefficients; and determining the correction coefficient by regression analysis of the obtained sets of the coefficients for the respective light intensities.

2. The optical measurement method according to claim 1, wherein the set of the coefficients comprises a coefficient of a linear term of the approximate equation and a coefficient of a quadratic term of the approximate equation, and the step of determining the correction coefficient comprises performing the regression analysis while the coefficient of the linear term is fixed as a value by using the output value from the detector with the first exposure time length within the first time range, which is used to determine an approximate equation corresponding to the first time range.

3. The optical measurement method according to claim 1, wherein the detector has a plurality of channels sectioned in units of a prescribed wavelength width, and the correction coefficient is determined for each channel.

4. The optical measurement method according to claim 1, wherein the detector comprises an indium gallium arsenide (InGaAs) linear image sensor.

5. An optical measurement apparatus comprising:

a detector having a detection sensitivity to at least a near-infrared region; and a controller configured to be able to refer to a correction coefficient, the controller being configured to:

obtain an output value by measuring a light sample with an exposure time length with the detector, the exposure time length including a first exposure time length within a predetermined time range and a second exposure time length not within the predetermined time range;

output the output value as it is, when the first exposure time length with which the output value is obtained is within a predetermined time range;

correct the output value with an amount of correction to output the corrected output value, when the second exposure time length with which the output value is obtained is not within the predetermined time range, the amount of correction comprising a value obtained by multiplying a coefficient by a square of the second exposure time length, the coefficient being determined based on the output value, the second exposure time length with which the output value is obtained, and the correction coefficient, obtain a plurality of output values by measuring a light sample having a prescribed light intensity at a plurality of exposure time lengths with the detector, the plurality of exposure time lengths comprising the first exposure time length within the predetermined time range and a plurality of second exposure time lengths not within the predetermined time range;

determine a set of the coefficients that define an approximate equation for the obtained plurality of output values;

vary the intensity of the light incident on the detector, and repeat the step of obtaining the plurality of output values and the step of determining the set of the coefficients; and determine the correction coefficient by regression analysis of the obtained sets of the coefficients for the respective light intensities.

* * * * *